United States Patent
Aldrich et al.

(10) Patent No.: US 11,510,964 B2
(45) Date of Patent: Nov. 29, 2022

(54) MACROCYCLIC PEPTIDES TO DECREASE C-MYC PROTEIN LEVELS AND REDUCE CANCER CELL GROWTH

(71) Applicants: University of Kansas, Lawrence, KS (US); University of Florida Research Foundation, Gainsville, FL (US)

(72) Inventors: Jane Aldrich, Gainsville, FL (US); Archana Mukhopadhyay, Cranbury, NJ (US); Laura E. Hanold, Gainsville, FL (US)

(73) Assignees: UNIVERSITY OF KANSAS, Lawrence, KS (US); UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 17/072,409

(22) Filed: Oct. 16, 2020

(65) Prior Publication Data
US 2021/0308210 A1 Oct. 7, 2021

Related U.S. Application Data

(63) Continuation of application No. 16/479,063, filed as application No. PCT/US2018/014595 on Jan. 20, 2018, now abandoned.

(60) Provisional application No. 62/448,823, filed on Jan. 20, 2017.

(51) Int. Cl.
| | |
|---|---|
| *A61K 38/12* | (2006.01) |
| *A61P 35/00* | (2006.01) |
| *A61K 9/00* | (2006.01) |
| *A61K 9/08* | (2006.01) |
| *A61K 47/02* | (2006.01) |

(52) U.S. Cl.
CPC ............ *A61K 38/12* (2013.01); *A61K 9/0019* (2013.01); *A61K 9/0029* (2013.01); *A61K 9/0053* (2013.01); *A61K 9/08* (2013.01); *A61K 47/02* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 5,885,959 A | * | 3/1999 | Hirai | A61P 25/30 514/18.3 |
| 6,248,363 B1 | * | 6/2001 | Patel | A61K 9/1676 424/497 |
| 10,259,843 B2 | * | 4/2019 | Aldrich | C07K 5/126 |
| 2002/0120099 A1 | | 8/2002 | Nishino et al. | |
| 2011/0190212 A1 | * | 8/2011 | Aldrich | A61K 31/409 514/17.6 |
| 2011/0195915 A1 | * | 8/2011 | Graham | C12Q 1/6886 514/21.1 |
| 2015/0202173 A1 | | 7/2015 | Gari et al. | |
| 2017/0369531 A1 | | 12/2017 | Zadina et al. | |

FOREIGN PATENT DOCUMENTS

| | | |
|---|---|---|
| WO | WO-2016/007956 A2 | 1/2016 |
| WO | WO-2016/061531 | 4/2016 |

OTHER PUBLICATIONS

Singleton et al. (Cancer. Aug. 15, 2015;121(16):2681-8) (Year: 2015).*
Fukuda et al. (J Neurochem. Sep. 1996;67(3):1309-16, abstract only) (Year: 1996).*
Communication pursuant to Rules 70(2) and 70a(2) EPC in EP Patent Application No. 18741702.7 dated Oct. 20, 2020 (1 page).
Deveza, et al., "Microfluidic Synthesis of Biodegradable Polyethylene-Glycol Microspheres for Controlled Delivery of Proteins and DNA Nanoparticles," ACS Biomater. Sci. Eng., 2015, vol. 1, pp. 157-165.
Extended European Search Report in EP Patent Application No. 18741702.7 dated Sep. 30, 2020 (8 pages).
Fukuda, et al., "Functional coupling of the delta-, mu-, and kappa-opioid receptors to mitogen-activated protein kinase and arachidonate release in Chinese hamster ovary cells," J. Neurochem., 1996, vol. 67, No. 3 (abstract only) (2 pages).
Gentilucci, et al., Molecular Docking of Opiates and Opioid Peptides, a Tool for the Design of Selective Agonists and Antagonists, and for the Investigation of Atypical Ligand-Receptor Interactions, Current Medicinal Chemistry, Apr. 1, 2012, vol. 19, No. 11, pp. 1587-1601.
International Preliminary Reporton Patentability in International Patent Application No. PCT/US2018/014595 dated Jul. 23, 2019 (9 pages).
International Search Report and Written Opinion in International Patent Application No. PCT/US2018/014595 dated May 15, 2018 (12 pages).
Maneckjee, et al., "Binding of Opioids to Human MCF-7 Breast Cancer Cells and Their Effects on Growth", Cancer Research, Apr. 15, 1990, vol. 50, No. 8, pp. 2234-2238.
Mukhopadhyay, et al., "Macrocyclic Peptides Decrease c-Myc Protein Levels and Reduce Prostate Cancer Cell Growth", Cancer Biology & Therapy, Aug. 3, 2017, vol. 18, No. 8, pp. 571-583.
Non-Final Office Action in U.S. Appl. No. 16/479,063 dated Apr. 17, 2020.
Restriction Requirement in U.S. Appl. No. 16/479,063 dated Feb. 7, 2020.

(Continued)

*Primary Examiner* — Sergio Coffa
(74) *Attorney, Agent, or Firm* — Foley & Lardner LLP

(57) ABSTRACT

The present technology provides methods end medicaments useful for treating prostate cancer and breast cancer. Such methods include administering at least one of cyclo[Phe-D-Pro-Phe-Trp] and cyclo[Phe-D-Pro-Phe-D-Trp] to a subject suffering from prostate cancer or breast cancer.

20 Claims, 35 Drawing Sheets
Specification includes a Sequence Listing.

(56) References Cited

OTHER PUBLICATIONS

Ross, et al., "Synthesis of CJ-15,208, a novel @k-opioid receptor antagonist", Tetrahedron Letters, Elsevier Ltd, Amsterdam, NL, Sep. 22, 2010, vol. 51, No. 38, pp. 5020-5023, XP027225957,SSN: 0040-4039 [retrieved on Aug. 18, 2010].
Singelton, et al., "The Mu Opioid Receptor: A New Target for Cancer Therapy?," Cancer, Aug. 15, 2015, vol. 121, No. 16, pp. 2681-2688.
Aldrich et al., "Alanine analogues of [D-Trp ]CJ-15,208: novel opioid activity profiles and prevention of drug- and stress-induced reinstatement of cocaine-seeking behaviour", British Journal of Pharmacology, 2014, vol. 171, pp. 3212-3222.
Aldrich et al., "Unexpected Opioid Activity Profiles of Analogues of the Novel Peptide Kappa Opioid Receptor Ligand CJ-15,208", ChemMedChem, 2011, vol. 6, pp. 1739-1745.
De Marco et al., "Versatile Picklocks to Access All Opioid Receptors: Tuning the Selectivity and Functional Profile of the Cyclotetrapeptide c[Phe-D-Pro-Phe-Trp] (CJ-15,208)", Journal of Medicinal Chemistry, 2016, vol. 59, pp. 9255-9261.
Extended European Search Report on EP Patent Application No. 19771690.5 dated Nov. 19, 2021, (11 pages).
International Preliminary Report on Patentability on PCT PCT/US2019/023698 dated Oct. 8, 2020 (8 pages).
International Search Report and Written Opinion in International Patent Application No. PCT/US2019/023698 dated Jun. 7, 2019 (16 pages).
Restriction Requirement dated in U.S. Appl. No. 16/982,638 dated Oct. 8, 2021 (11 pages).
Communication Pursuant to Article 94(3) dated EP 18741702.7 dated Aug. 2, 2021 (4 pages).

\* cited by examiner

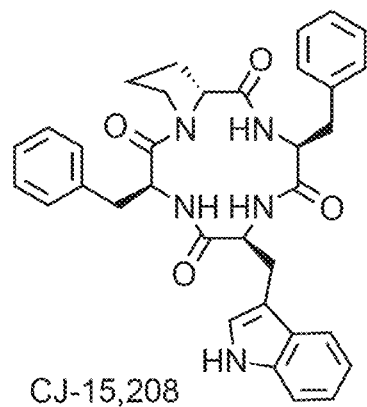
CJ-15,208
FIG. 1A
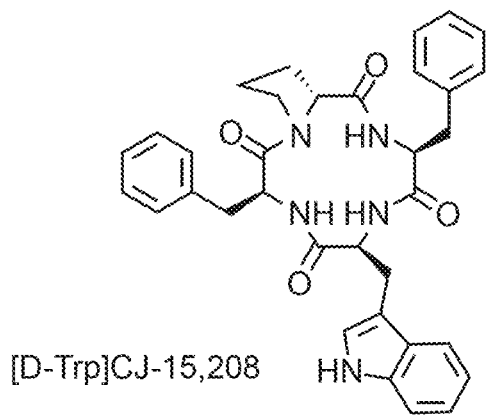
[D-Trp]CJ-15,208
FIG. 1B
H₂N-Tyr-Gly-Gly-Phe-Leu-Arg-Arg-Ile-Arg-Pro-Lys-Pro
Dynorphin A (1-13)
FIG. 1C
N-Bn-Tyr-Gly-Gly-Phe-D-Asp-Arg-Arg-Dap-Arg-Pro-Lys-NH₂
Zyklophin
FIG. 1D

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ctggtgctcc atgaggag                                                 18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
aggtgatcca gactctgac                                                19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ccatggagaa ggctgggg                                                 18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
caaatgtgtc atggatgacc                                               20

<210> SEQ ID NO 5
<211> LENGTH: 12
<212> TYPE: PRT
<213> ORGANISM: Unknown
<220> FEATURE:
<223> OTHER INFORMATION: Description of Unknown: Dynorphin A sequence

<400> SEQUENCE: 5

Tyr Gly Gly Phe Leu Arg Arg Ile Arg Pro Lys Pro
1               5                   10

MACROCYCLIC PEPTIDES TO DECREASE C-MYC PROTEIN LEVELS AND REDUCE CANCER CELL GROWTH

CROSS-REFERENCE TO RELATED APPLICATIONS

This application is a continuation of U.S. patent application Ser. No. 16/479,063, filed on Jul. 18, 2019, which is a U.S. National Phase Patent Applicader 35 U.S.C. § 371 of International Application No. PCT/US2018/014595, filed on Jan. 20, 2018, which claims the benefit of and priority to U.S. Provisional Patent Application No. 62/448,823, filed on Jan. 20, 2017, the entire disclosures of which are incorporated herein by reference for any and all purposes.

U.S. GOVERNMENT LICENSE RIGHTS

This invention was made with government support under grant number W81XWH-14-1-0330 awarded by the Department of Defense. The government has certain rights in the invention.

SEQUENCE LISTING

The instant application contains a Sequence Listing which has been submitted electronically in ASCII format and is hereby incorporated by reference in its entirety. Said ASCII copy, created on Jun. 23, 2021, is named 104434-0236_SL.txt and is 1,498 bytes in size.

FIELD

The present technology generally relates to methods and medicaments useful for treating prostate cancer and breast cancer.

SUMMARY

In an aspect, a method is provided where the method includes administering at least one of cyclo[Phe-D-Pro-Phe-Trp] and cyclo[Phe-D-Pro-Phe-D-Trp] to a subject suffering from prostate cancer or breast cancer. In any embodiment herein, the method may include administering an effective amount of at least one of cyclo[Phe-D-Pro-Phe-Trp] and cyclo[Phe-D-Pro-Phe-D-Trp] to the subject.

In a related aspect, the present technology provides at least one of cyclo[Phe-D-Pro-Phe-Trp] and cyclo[Phe-D-Pro-Phe-D-Trp] for use in a medicament for the treatment of prostate cancer or breast cancer in a subject. The medicament may include an effective amount of at least one of cyclo[Phe-D-Pro-Phe-Trp] and cyclo[Phe-D-Pro-Phe-D-Trp].

DESCRIPTION OF THE DRAWINGS

FIGS. 1A-1D illustrates the peptide structures evaluated for effect on c-Myc in the working examples, where FIG. 1A provides the structure for macrocyclic tetrapeptide cyclo[Phe-D-Pro-Phe-Trp] ("CJ-15,208"); FIG. 1B provides the structure for macrocyclic tetrapeptide cyclo[Phe-D-Pro-Phe-D-Trp] ("[D-Trp]CJ-15,208"); FIG. 1C illustrates dynorphin A-(1-13) (SEQ ID NO: 5); and FIG. 1D illustrates zyklophin.

10A shows p-Erk/total Erk protein levels in PC-3 cells, FIG. 10B shows p-Akt/total Akt protein levels in PC-3 cells, and FIG. 10C shows p-PP2A/total PP2A protein levels in PC-3 cells, according to the working examples.

DETAILED DESCRIPTION

Figure 1E:
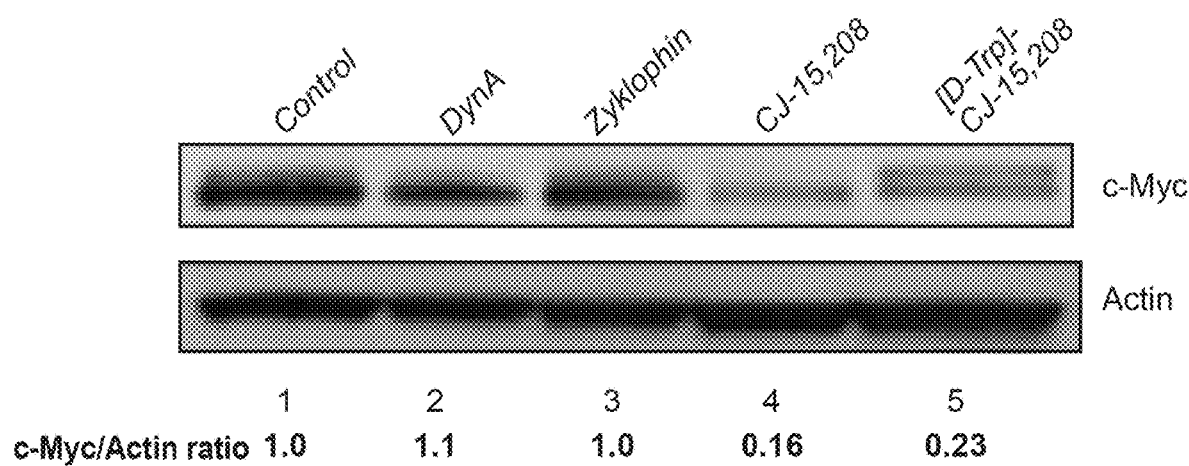
FIG. 1E illustrates the western blot analysis of cellular c-Myc treated with 0.5% DMSO (lane 1), 1 µM dynorphin (lane 2), 10 µM zyklophin (lane 3), 50 µM CJ-15,208 (lane 4), and 50 µM [D-Trp]CJ-15,208 (lane 5), according to the working examples.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

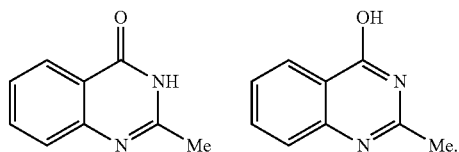 [SMILES: Cc1nc2ccccc2c(=O)[nH]1 ; Cc1nc(O)c2ccccc2n1]

As another example, guanidines may exhibit the following isomeric forms in protic organic solution, also referred to as tautomers of each other:

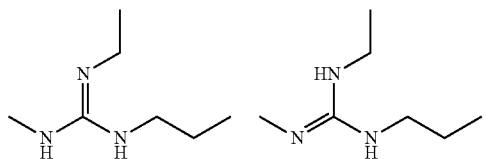

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which this invention pertains.

The Present Technology

Current therapies such as androgen deprivation therapy or the application of androgen receptor antagonists are initially effective in treating prostate cancer (PC), but the disease generally recurs with metastasis due to non-responsiveness to these treatments.[1-3] These therapies lower the level of the androgens testosterone and dihydrotestosterone or interfere with the binding of androgen ligands to androgen receptors (AR), respectively,[4] but the disease typically progresses despite application of these treatments, with the AR typically being expressed in truncated or mutated form.[5] Although the mechanism for cancer progression after androgen deprivation/AR antagonist treatment is not fully understood, possible explanations include: i) AR gene amplification, ii) constitutive activation of AR, iii) AR mutation or truncation, iv) activation of AR by growth factors, and/or v) activation of AR by alternative androgen independent signaling pathways.[5,6]

The oncoprotein c-Myc is a transcription factor that is overexpressed in most cancer types.[5,7-10] It accumulates and is stabilized by phosphorylation as phospho-Ser62-c-Myc.[11-13] c-Myc is upregulated in both androgen receptor positive and androgen receptor negative, ligand-independent castration resistant prostate cancers,[5,14-16] and recent studies have shown that the androgen receptor directly regulates c-Myc protein levels in an androgen independent manner.[5,14,17]

c-Myc is overexpressed in 30-50% of high grade breast cancer tumors, and activation of c-Myc has been reported in breast cancer progression. Evidence indicates that c-Myc overexpression contributes to developing resistance to hormonal therapy in estrogen receptor (ER) positive tumors. c-Myc expression is also elevated in triple negative breast cancer (TNBC) compared to tumors expressing ER or HER2, and c-Myc overexpression in TNBC correlates with a poor prognosis.

The present technology provides methods and medicaments that use at least one of cyclo[Phe-D-Pro-Phe-Trp] and cyclo[Phe-D-Pro-Phe-D-Trp] to treat prostate cancer and breast cancer. As provided herein, both of these macrocyclic peptides (also referred to as "compounds of the present technology") surprisingly induced cytotoxicity and lowered c-Myc protein levels in several cancer cell lines, evidencing their viability as treatments for prostate and breast cancers.

Thus, in an aspect, a method is provided where the method includes administering at least one of cyclo[Phe-D-Pro-Phe-Trp] and cyclo[Phe-D-Pro-Phe-D-Trp] or a pharmaceutically acceptable salt thereof to a subject suffering from prostate cancer or breast cancer. In any embodiment herein, the method may include administering an effective amount of at least one of cyclo[Phe-D-Pro-Phe-Trp] and cyclo[Phe-D-Pro-Phe-D-Trp] or a pharmaceutically acceptable salt thereof to the subject. In any embodiment herein, it may be that the prostate cancer exhibits levels of c-Myc significantly greater than levels of c-Myc in normal prostate cells. The prostate cancer of any embodiment herein may include at least one oncogenic mutation found in a PC-3 cell line, a LNCaP cell line, a 22Rv1 cell line, a DU145 cell line, or a combination of any two or more thereof (also stated as "the prostate cancer comprises a PC-3 cell line, a LNCaP cell line, a 22Rv1 cell line, a DU145 cell line, or a combination of any two or more thereof"). The prostate cancer of any embodiment herein may include at least about 25%, at least about 50%, at least about 75%, or about 100% of oncogenic mutations found in a PC-3 cell line, a LNCaP cell line, a 22Rv1 cell line, a DU145 cell line, or a combination of any two or more thereof. In any embodiment herein, it may be that the breast cancer exhibits levels of c-Myc significantly greater than levels of c-Myc in normal breast cells. The breast cancer of any embodiment herein may include triple negative breast cancer. The breast cancer of any embodiment herein may include at least one oncogenic mutation found in a BT-20 cell line, a MDA-MB-468 cell line, a MDA-MB-231 cell line, a MCF-7 cell line, a SKBR-3 cell line, a BT-474 cell line, or a combination of any two or more thereof. The breast cancer of any embodiment herein may include at least about 25%, at least about 50%, at least about 75%, or about 100% of oncogenic mutations found in a BT-20 cell line, a MDA-MB-468 cell line, a MDA-MB-231 cell line, a MCF-7 cell line, a SKBR-3 cell line, a BT-474 cell line, or a combination of any two or more thereof. Administering at least one of cyclo[Phe-D-Pro-Phe-Trp] and cyclo[Phe-D-Pro-Phe-D-Trp] or a pharmaceutically acceptable salt thereof may occur multiple times a day, about twice a day, once a day, about five times a week, about four times a week, about three times a week, about twice a week about once a week, about twice a month, or any range including and/or in between any two of these values.

The method of any embodiment herein may include administering a composition where the composition includes at least one of cyclo[Phe-D-Pro-Phe-Trp] and cyclo[Phe-D-Pro-Phe-D-Trp] (or a pharmaceutically acceptable salt thereof) and a pharmaceutically acceptable carrier; the method of any embodiment herein may include administering a medicament that includes at least one of cyclo[Phe-D-Pro-Phe-Trp] and cyclo[Phe-D-Pro-Phe-D-Trp] (or a pharmaceutically acceptable salt thereof).

Thus, present technology also provides compositions (e.g., pharmaceutical compositions) and medicaments that include at least one of cyclo[Phe-D-Pro-Phe-Trp] and cyclo[Phe-D-Pro-Phe-D-Trp] (or a pharmaceutically acceptable salt thereof) and a pharmaceutically acceptable carrier (such as one or more excipients or fillers). The compositions may be used in the methods and treatments described herein. The pharmaceutical composition may include an effective amount of at least one of cyclo[Phe-D-Pro-Phe-Trp] and cyclo[Phe-D-Pro-Phe-D-Trp] (or a pharmaceutically acceptable salt thereof). In any embodiment herein, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of prostate cancer or breast cancer. Another example of an effective amount includes amounts or dosages that yield acceptable toxicity and bioavailability levels for therapeutic (pharmaceutical) use including, but not limited to, prostate cancer or breast cancer. Another example of an effective amount includes amounts or dosages that are capable of reducing symptoms associated with prostate cancer or breast cancer, such as, for example, reduction in proliferation and/or metastasis of the cancer. The effective amount may be from about 0.01 µg to about 100 mg of the compound per gram of the composition, and preferably from about 0.1 µg to about 500 µg of the compound per gram of the composition. As used herein, a "subject" or "patient" is a mammal, such as a cat, dog, rodent or primate. Typically the subject is a human, and, preferably, a human suffering from or suspected of suffering from prostate cancer or breast cancer. The term "subject" and "patient" can be used interchangeably.

In any of the embodiments of the present technology described herein, the pharmaceutical composition may be packaged in unit dosage form. The unit dosage form is effective in treating prostate cancer or breast cancer. Generally, a unit dosage including at least one of cyclo[Phe-D-Pro-Phe-Trp] and cyclo[Phe-D-Pro-Phe-D-Trp] (or a pharmaceutically acceptable salt thereof) will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising at least one of cyclo[Phe-D-Pro-Phe-Trp] and cyclo[Phe-D-Pro-Phe-D-Trp] (or a pharmaceutically acceptable salt thereof) may vary from $1 \times 10^{-4}$ g/kg to 1 g/kg, preferably, $1 \times 10^{-3}$ g/kg to 1.0 g/kg. Dosage of a compound of the present technology may also vary from 0.01 mg/kg to 100 mg/kg or, preferably, from 0.1 mg/kg to 10 mg/kg. For example, the dosage may be about 1 mg to about 150 mg of the at least one of cyclo[Phe-D-Pro-Phe-Trp] and cyclo[Phe-D-Pro-Phe-D-Trp] per kilogram of the subject; in any embodiment of a method of a method of the present technology, the method may include administering to the subject about 1 mg/kg to about 150 mg/kg of the at least one of cyclo[Phe-D-Pro-Phe-Trp] and cyclo[Phe-D-Pro-Phe-D-Trp]. Thus, the dosage/administration of at least one of cyclo[Phe-D-Pro-Phe-Trp] and cyclo[Phe-D-Pro-Phe-D-Trp] may be about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 12 mg/kg, about 14 mg/kg, about 16 mg/kg, about 18 mg/kg, about 20 mg/kg, about 22 mg/kg, about 24 mg/kg, about 26 mg/kg, about 28 mg/kg, about 30 mg/kg, about 32 mg/kg, about 34 mg/kg, about 36 mg/kg, about 38 mg/kg, about 40 mg/kg, about 42 mg/kg, about 44 mg/kg, about 46 mg/kg, about 48 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 110 mg/kg, about 120 mg/kg, about 130 mg/kg, about 140 mg/kg, about 150 mg/kg, or any range including and/or in between any two of these values.

Suitable unit dosage forms, include, but are not limited to powders, tablets, pills, capsules, lozenges. suppositories. patches. nasal sprays, injectibles, implantable sustained-release formulations, rnucoadherent films, topical varnishes, lipid complexes, etc. For example, in any embodiment herein of the present technology, at least one of cyclo[Phe-D-Pro-Phe-Trp] and cyclo[Phe-D-Pro-Phe-D-Trp] may be included in a liquid formulation (such as an injectable formulation, an intravenous formulation, a subcutaneous formulation, and/or an oral liquid formulation) that includes about 0.1 mg/mL (i.e., 0.1 mg compound per 1 mL liquid formulation) to about 50 mg/mL of the at least one of cyclo[Phe-D-Pro-Phe-Trp] and cyclo[Phe-D-Pro-Phe-D-Trp]. Thus, the liquid formulation may include the at least one of cyclo[Phe-D-Pro-Phe-Trp] and cyclo[Phe-D-Pro-Phe-D-Trp] at about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 12 mg/mL, about 14 mg/mL, about 16 mg/mL, about 18 mg/mL, about 20 mg/mL, about 22 mg/mL, about 24 mg/mL, about 26 mg/mL, about 28 mg/mL, about 30 mg/mL, about 32 mg/mL, about 34 mg/mL, about 36 mg/mL, about 38 mg/mL, about 40 mg/mL, about 42 mg/mL, about 44 mg/mL, about 46 mg/mL, about 48 mg/mL, about 50 mg/mL, or any range including and/or in between any two of these values.

The pharmaceutical compositions may be prepared by mixing at least one of cyclo[Phe-D-Pro-Phe-Trp] and cyclo[Phe-D-Pro-Phe-D-Trp], pharmaceutically acceptable salts thereof, tautomers thereof, or solvates thereof, with one or more pharmaceutically acceptable carriers, excipients, binders, diluents or the like to prevent and treat disorders associated with prostate cancer and/or breast cancer. cyclo[Phe-D-Pro-Phe-Trp] and cyclo[Phe-D-Pro-Phe-D-Trp] (or a pharmaceutically acceptable salt thereof) may be used to prepare formulations and medicaments that treat prostate cancer and/or breast cancer. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections.

The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing at least one of cyclo[Phe-D-Pro-Phe-Trp] and cyclo[Phe-D-Pro-Phe-D-Trp], or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, and/or emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers, and combinations of any two or more thereof. The carriers and stabilizers may vary and may include one or more of nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols.

For example, in any embodiment of the present technology disclosed herein, the pharmaceutically acceptable carrier may include one or more of a polyethylene glycol, a polyethylene glycol fatty acid monoester, a polyethoxylene sorbitan monoester, or a combination of any two or more thereof.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also include, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs.

Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebotreated or other suitable control subjects.

In an aspect, a method for inhibiting cell motility of a cancer cell is provided. The method includes contacting the cancer cell with a compound of the present technology (or a pharmaceutically acceptable salt thereof), thereby inhibiting the cell motility of the cancer cell. The method may include contacting the cell with an effective amount of a compound of the present technology (or a pharmaceutically acceptable salt thereof). In the method, the effective amount may include an amount effective in reducing cell motility of the cancer cell, e.g., as compared to cell motility of the cancer cell in the absence of the compound of the present technology and/or other motility-reducing compounds. For instance, the effective amount may include an amount effective in reducing cell motility of the cancer cell by at least about 50%, at least about 60%, at least about 70%, at least about 80%, at least about 90%, or at least about 95% as compared to cell motility of the cancer cell in the absence of the compound of the present technology and/or other motility-reducing compounds. The method may include inhibiting metastasis of the cancer cell. The cancer cell may include a breast cancer cell or prostate cancer cell of any embodiment described herein. The contacting may or may not be within a patient and/or on a patient. For example, the contacting may occur in vitro. In any of the embodiments of the method, the contacting step may include administration of a pharmaceutical composition, where the pharmaceutical composition includes an effective amount of a compound of the present technology (or a pharmaceutically acceptable salt thereof) and a pharmaceutically acceptable carrier.

The examples herein are provided to illustrate advantages of the present technology and to further assist a person of ordinary skill in the art with preparing or using the present technology. The examples herein are also presented in order to more fully illustrate preferred aspects of the present technology. The examples should in no way be construed as limiting the scope of the present technology, as defined by the appended claims. The examples can include or incorporate any of the variations, aspects or aspects of the present technology described above. The variations, embodiments, or aspects described above may also further each include or incorporate the variations of any or all other variations, embodiments, or aspects of the present technology.

EXAMPLES

Exemplary Synthetic Procedures and Characterization
Cell Lines and Cell Culture Conditions.

Human prostate cancer PC-3 cells were cultured and maintained in EMEM (ATCC), non-prostate HEK (human embryonic kidney) cells were cultured in DMEM, human prostate cancer DU145, LNCaP, 22Rv1 cells were cultured in RPMI 1640 (ATCC), and normal BPH-1 prostate cells and prostate cancer C4-2 cell line were cultured in RPMI 1640 (ATCC), all containing 10% fetal bovine serum (Atlanta Biologicals) and 1% penicillin/streptomycin (Invitrogen). Cells were grown at 37° C. in humidified air with 5% $CO_2$ and passaged every fourth to fifth day following trypsinization with trypsin/EDTA (Invitrogen).[16]

Cell Proliferation Assay.

PC-3, LNCaP, DU 145, 22Rv1, C4-2, BPH-1, and HEK cells were grown to a density of 2000 cells/well in 96 well plates and treated with [D-Trp]CJ-15,208 or other peptides for 24-72 h in duplicate. Media containing [D-Trp]CJ-15, 208 was changed every 24 h. The proliferation of treated cells was determined using the cell proliferation reagent WST-1 (Roche) per the manufacturer's instructions and compared to treated control cells in 1% DMSO in media. After treatment with compound 10 µL of the reagent was added to the well in 100 µL culture media, and the cells incubated at 37° C. for 30 min. The absorbance of the media in each well was measured at 410 nm using a plate reader (BioTek). The percentage cell proliferation was normalized to vehicle treated control cells calculated as: (mean absorbance of sample/mean absorbance of control cells)×100.[38]

Cell Viability Assay.

The viability of prostate cancer cells was determined using Trypan Blue (Sigma) per the manufacturer's instructions. Cells were grown in 6 well plates to a density of $1\times10^5$ cells/well to 75% confluency and treated with compound in 0.5% DMSO at the indicated concentrations for 24-72 h, with 0.5% DMSO as the vehicle control. After treatment, the cell media from each well was collected. The cells were washed with phosphate buffer saline (PBS), trypsinized, and collected. All of the cells, combined media, and washes were centrifuged at 250×g for 5 min. The supernatant was discarded, and the cell pellet was resuspended in 500 µL PBS. Trypan blue (10 µL) was added to 100 µL of resuspended cells, and the solution incubated for 10 min. The cell number in 10 µL was then counted using a hematocytometer. Viable cells (not stained) were distinguished from dead cells (colored blue) and the % viable cells calculated as follows: [(number of white cells)/(number of total cells (white+ blue))]*100 and compared with untreated cells.[16]

Western Blot Analysis.

Cells were seeded in 6 well plates at a density of $1\times10^5$ cells/well and grown to 75% confluence. Cells were treated with [D-Trp]CJ-15,208 at the indicated concentrations. Cells were then harvested as described above, and the cell pellets lysed in RIPA buffer consisting of 10 mM Tris HCl, pH 8.0, 150 mM NaCl, 1 mM EDTA, 1% Triton-X-100, 0.1% SDS, 1% sodium deoxycholate, and a protease inhibitor cocktail #P8340 (Sigma). Cell lysates were centrifuged at 13×1000 rpm for 15 min and the supernatants collected. The total protein concentration was measured in cell lysates using the standard Bradford assay. SDS gel electrophoresis was performed using 4-20% polyacrylamide gel (BioRad). Western blot analysis was performed using the following antibodies: i) c-Myc #5605 (rabbit monoclonal, 1:2000 dilution, (Cell Signaling Technologies)); actin #A2228 (mouse monoclonal, 1:5000 dilution (Sigma)), PP2A #610555 (mouse monoclonal 1:5000 dilution, BD Biosciences), p-PP2A #1155-1 (rabbit polyclonal, 1:5000 dilution (Epitomics)), Erk #9107 (mouse monoclonal, 1:2000 dilution (Cell Signaling Technologies) and p-Erk #4376 (rabbit monoclonal, 1:2000 (Cell Signaling Technologies)); Akt #2920 (mouse monoclonal, 1:2000 dilution (Cell Signaling Technologies)), p-Akt #4056 (rabbit monoclonal, 1:2000 (Cell Signaling Technologies)). The secondary antibodies, goat-anti-mouse #116-035-003 and goat-anti-rabbit #111-035-003, were obtained from Jackson ImmunoResearch Laboratory. Signal densities of the protein bands were determined using ImageJ software (NIH) and normalized to the internal loading control (actin).

Cell Cycle Analysis.

PC-3 cells were grown in T-75 flask to 75% confluency and treated with either 10 μM [D-Trp]CJ-15,208 in 0.5% DMSO or 0.5% DMSO as a vehicle control for 24-48 h. After treatment, the cell media was collected, the cells were washed with ice cold PBS twice, and the washes collected with the media. The cells were then trypsinized and the combined cells and media centrifuged at 1200 rpm for 5 min. The cell pellet was resuspended in PBS, the cells counted using a hematocytometer, and 1 million cells resuspended in 300 μL PBS. The cells were fixed with 700 μL ice cold 100% ethanol overnight and then centrifuged at 1200 rpm. Following removal of the ethanol, the cells were resuspended in 500 μL PBS containing 100 μg/mL RNAse and incubated for 30 min at room temperature. Propidium iodide (PI) solution (Sigma, 100 μg/mL) was added, and the solution then incubated for 30 min at room temperature in the dark. Cell cycle analysis[38] was performed using a Beckman-Coulter MoFlo XDP flow cytometer, and the cell cycle phase distribution was analyzed using FlowJo v10.1.

Annexin V-APC/PI Assay.

The extent of apoptosis was analyzed by detecting surface expression of phosphatidylserine on apoptotic cells using an Annexin V-APC/PI dual staining apoptosis detection kit I (BD Biosciences) according to the manufacturer's protocol. Following treatment of PC-3 cells with 10 μM [D-Trp]CJ-15,208 or vehicle for 24 h or 48 h, the cells were collected, washed twice with cold PBS, and resuspended in 1× binding buffer at a concentration of $1 \times 10^6$ cells/mL. Cell suspension (100 μL) was transferred to a 5 ml culture tube, and 5 μL of Annexin V-APC and 25 μL of PI (50 μg/mL) were added. The cells were incubated for 15 min at room temperature in the dark with gentle vortexing, 400 μL of 1× binding buffer was then added to each sample, and the samples were analyzed using a Beckman-Coulter MoFlo XDP flow cytometer within one hour. The number of viable, apoptotic and necrotic cells were quantified using FlowJo v10.0.7. The apoptosis fraction (%) was calculated as (number of apoptotic cells/the number of total cells observed)×100%.[38]

c-Myc mRNA Measurement.

PC-3 cells were grown in 10 cm petri dishes to 75% confluency, and then treated with [D-Trp] CJ-15,208 (10 μM) for 2-48 h. Cells were harvested and the total RNA from each sample was isolated using the Aurum Total RNA Mini Kit #732-6820 (Bio-Rad) per the manufacturer's instructions. The RNA concentration in the sample was determined using a NanoDrop ND-1000 spectrophotometer. Total RNA (1 μg) from each sample was used to synthesize cDNA using the iScript cDNA Synthesis Kit (BioRad). Real-time PCR was performed with a Power-SYBR Green PCR Master Mix (Applied Biosystems) using the following thermal cycles: initial activation at 95° C. for 5 min, followed by 40 cycles of 95° C. for 15 s and 60° C. for 1 min. The fluorescence was determined at the melting temperature of the product for 20 s (ABI PRISM 7000 Sequence Detection System, Applied Biosystems). The following primer sets were used to amplify regions of c-Myc and GAPDH (internal control): c-Myc (forward: 5'-CTG GTG CTC CAT GAG GAG-3' (SEQ ID NO: 1), reverse: 5'-AGG TGA TCC AGA CTC TGA C-3' SEQ ID NO: 2)) and GAPDH (forward: 5'-CCA TGG AGA AGG CTG GGG-3' (SEQ ID NO: 3), reverse: 5'-CAA ATG TGT CAT GGA TGA CC-3' SEQ ID NO: 4)). The levels of c-Myc mRNA were normalized to the GAPDH mRNA levels.[37]

c-Myc Knockdown.

PC-3 cells were seeded at a density of $2 \times 10^6$ cells in 10 cm plates and grown to 75-85% confluence in EMEM supplemented with 10% FBS and penicillin/streptomycin. The media was then replaced with antibiotic free EMEM containing 10% FBS, and the cells were incubated for a minimum of 12 h. Solutions containing 500 nM siRNA against c-Myc #L-003292-02-0005, 500 nM non-targeting siRNA #D-001810-10-05, or 5% (v/v) dharmafect 2 #T-2002-02 (Dharmacon) were prepared in optiMEM with Glutamax (Gibco) to obtain a final volume of 1 mL each. After incubating 5 min at room temperature, the siRNA and dharmafect solutions were combined and incubated for an additional 20 min at room temperature. The transfection complex was then added to the cells in fresh antibiotic free EMEM containing 10% FBS, and the cells were incubated for 24 h. The cells were split into two 10 cm tissue culture dishes in EMEM supplemented with 10% FBS and penicillin/streptomycin, and allowed to adhere for another 24 h. The cells were treated with 10 μM [D-Trp]CJ-15,208 or 0.5% DMSO vehicle control for a total of 48 h. The cells were then collected and prepared for the Annexin V-APC/PI assay as described above. Samples were analyzed using a BD FACSCanto-II cell analyzer and quantified in FlowJo v10.2.

c-Myc Overexpression.

Forced expression of c-Myc in HEK 293 cells was performed using X-temeGENE HP #6366244001 (Sigma). Cells were cultured in antibiotic free DMEM supplemented with 10% FBS and transfected with pcDNA3-HA-HA-c-Myc #74164 (Addgene). Empty-vector pcDNA3-EV was used as a control. Transfected cells were selected with 500 μg/mL G418 for 2 weeks. The transfected cells were then seeded onto 10 cm tissue culture plates and allowed to grow to 75% confluence in DMEM supplemented with 10% FBS and penicillin/streptomycin. The cells were treated with 10 μM [D-Trp]CJ-15,208 or 0.5% DMSO vehicle control for a total of 48 h, after which the cells were collected and prepared for the Annexin V-APC/PI assay as described above. Samples were analyzed using a BD FACSCanto-II cell analyzer and quantified in FlowJo v10.2.

Statistical Analysis.

Each experiment was performed in triplicate unless otherwise stated in the figure legend. GraphPad Prism 5 was used to determine $IC_{50}$ values. Data represent the mean value+/−SEM. Compound vs. vehicle treated cells in the cell cycle phase and apoptosis experiments (FIGS. 5-8) were compared using the student's t-test, with a two-tailed, unpaired method, using the Prism software. The effects of compound vs. vehicle treatment on protein levels (FIG. 10) were evaluated by one-way ANOVA with Dunnett's test for multiple comparisons.

Results

Figure 1F:
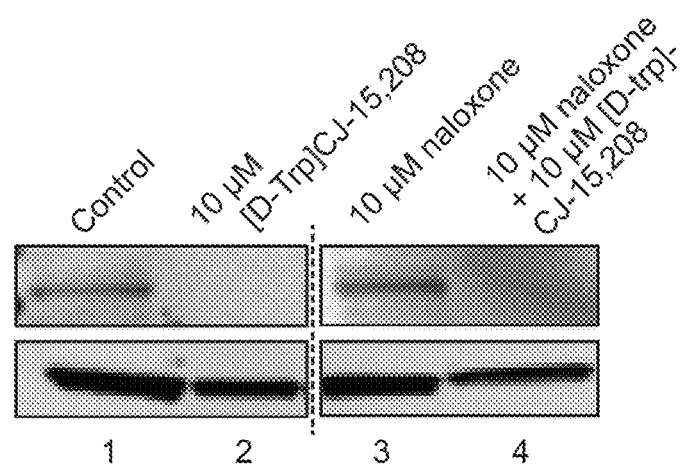
FIG. 1F illustrates the western blot analysis of c-Myc protein leels in PC-3 cells after treatment with 10 µM of naloxone and/or 10 µM [D-Trp]CJ-15,208, according to the working examples.

Many cancer cells, including prostate cancer cells, over-express c-Myc.[9,30] The effect of several kappa opioid receptor (KOR) ligands were examined, including the macrocyclic tetrapeptides CJ-15,208 and [D-Trp]CJ-15,208 (FIGS. 1 A and B), the endogenous KOR agonist dynorphin A (Dyn A, FIG. 1C),[28] and the KOR antagonist zyklophin (FIG. 1D),[31] on cellular c-Myc protein levels. The cellular levels of c-Myc protein decreased 5-fold (FIG. 1E, lanes 4 and 5) following treatment with CJ-15,208 and [D-Trp]CJ-15,208, but were not decreased by treatment with dynorphin A or its antagonist analog zyklophin (FIG. 1E, lanes 2 and 3). A radioligand binding assay for KOR, performed under standard conditions using [$^3$H]diprenorphine (and Dyn A-(1-13) amide to determine nonspecific binding[32]), showed no detectable specific KOR binding to PC-3 cells. PC-3 cells were treated with 10 μM of the nonselective opioid antagonist naloxone for 48 h, which showed no effect on c-Myc protein levels (FIG. 1F, lane 3), and did not alter the decrease in c-Myc protein levels caused by [D-Trp]CJ-15,208 (lane 4 vs. lane 2). These results demonstrate the effect of these cyclic tetrapeptides have on c-Myc in the prostate cancer cells is not mediated through KOR.

Figure 2A:
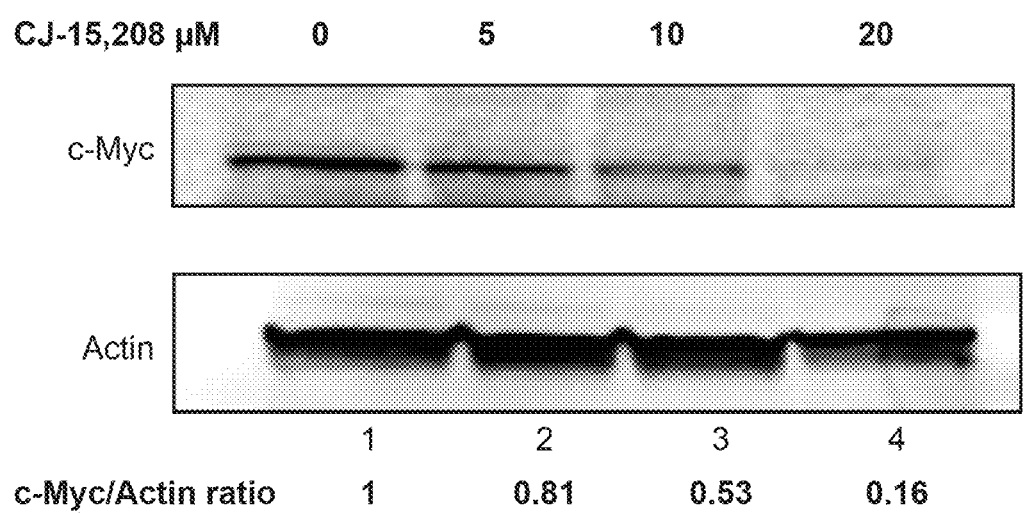
FIGS. 2A and 2B illustrate the western blot analysis showing c-Myc protein levels after 48 h treatment of PC-3 cells with 0 µM, 5 µM, 10 and 20 µM of CJ-15,208 and [D-Trp]CJ15,208, respectively, where FIG. 2A provides the western blot analysis for CJ-15,208 and FIG. 2B provides the western blot analysis for [D-Trp]CJ-15,208 as well as a histogram of the data, according to the working examples.
Figure 2B:
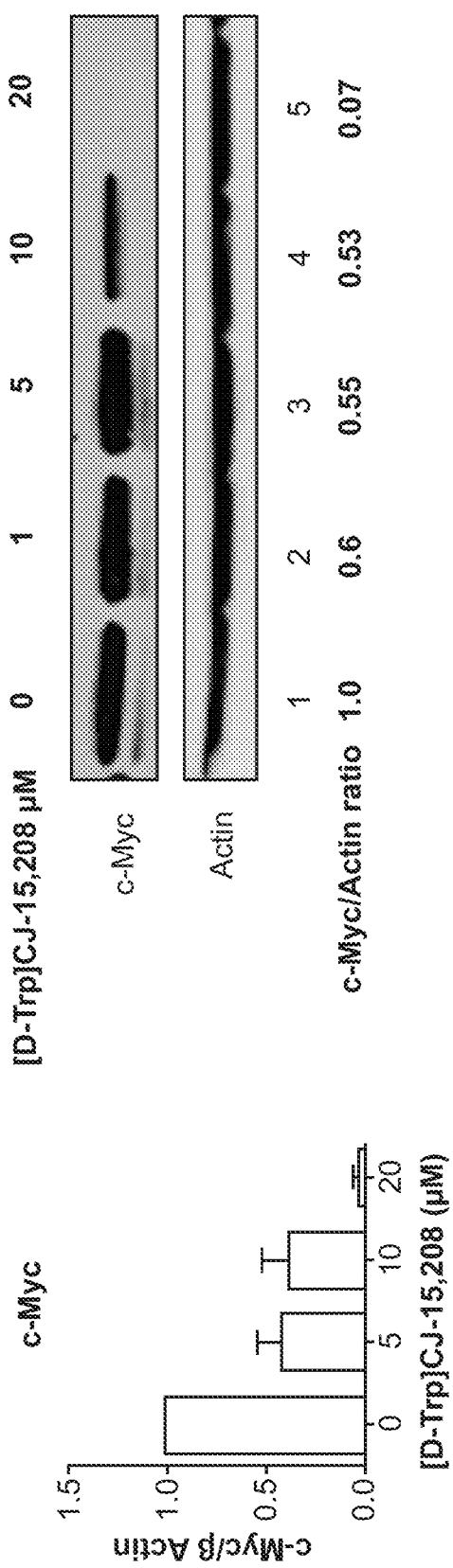
Figure 2C:
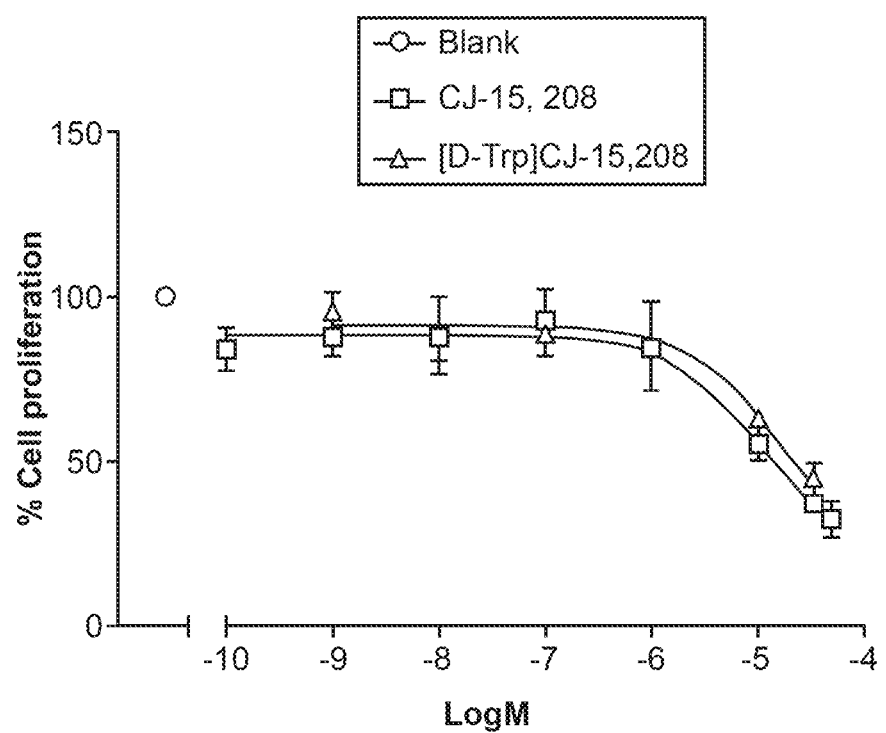
FIG. 2C provides a graph illustrating the results of a cell proliferation assessment using WST-1 following treatment with CJ-15,208 and[D-Trp]CJ-15,208 for 48 h, according to the working examples.
Figure 2D:
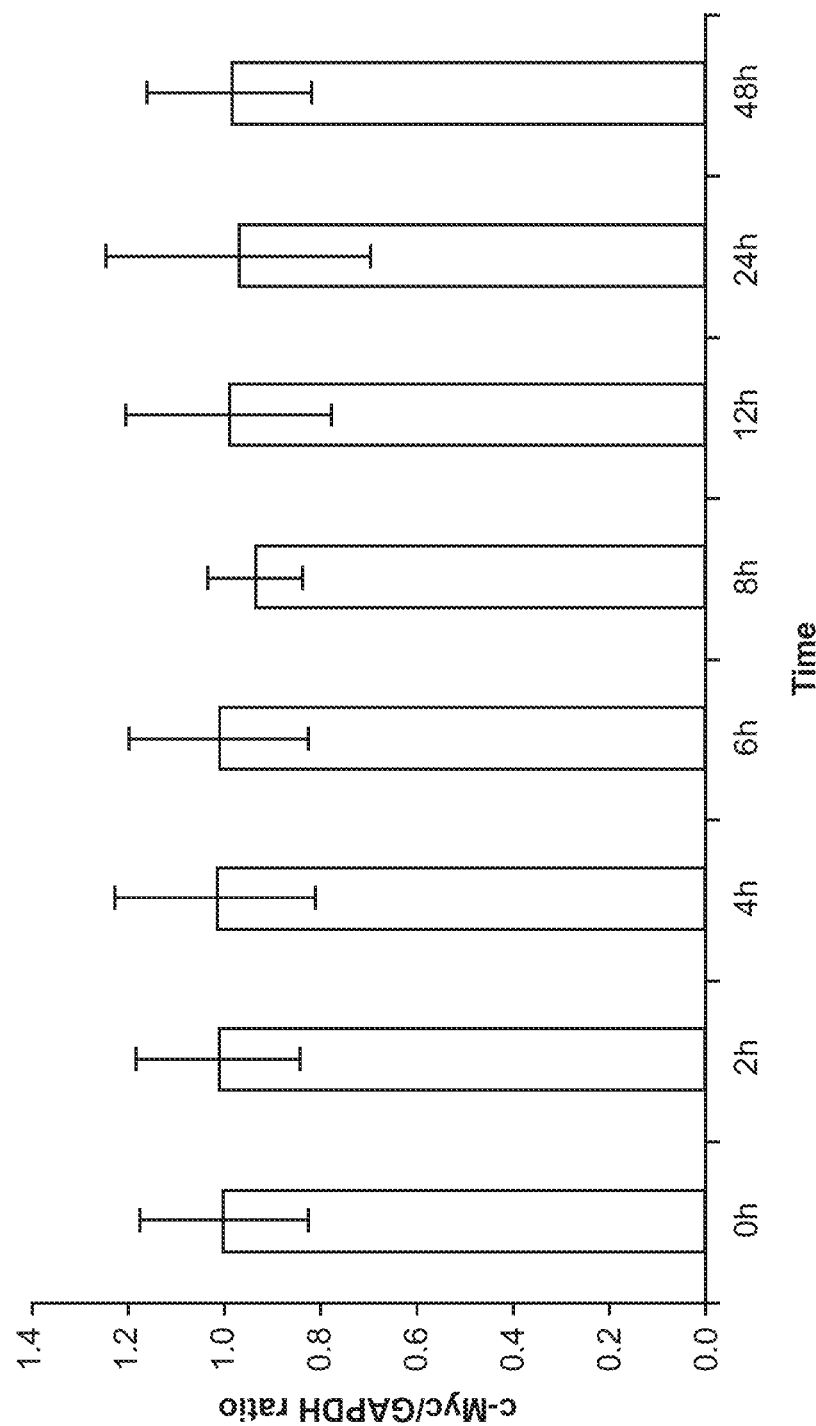
FIG. 2D provides a graph showing c-Myc mRNA expression in PC-3 cells following treatment with 10 µM [D-Trp]CJ-15,208 for 0-48 h, according to the working examples.

Both [D-Trp]CJ-15,208 and CJ-15,208 reduced c-Myc protein levels in PC-3 cells in a concentration dependent manner after 48 h treatment (FIGS. 2A and 2B), causing an approximately 50% reduction at 10 μM (FIG. 2A, lane 3, and FIG. 2B, lane 4). CJ-15,208 and [D-Trp]CJ-15,208 demonstrated reduced cell proliferation in PC-3 cells after 48 h, exhibiting $IC_{50}$ values of 10.1±0.9 μM and 16.5±0.7 μM for CJ-15,208 and [D-Trp]CJ-15,208, respectively (FIG. 2C). Treatment of PC-3 cells with 10 μM of [D-Trp]CJ-15,208 for 0 h to 48 h did not affect mRNA expression at any time point (FIG. 2D). These results indicate that [D-Trp]CJ-15,208 decreases c-Myc protein levels in these cancer cells, but does not affect c-Myc gene transcription.

Figure 3A:
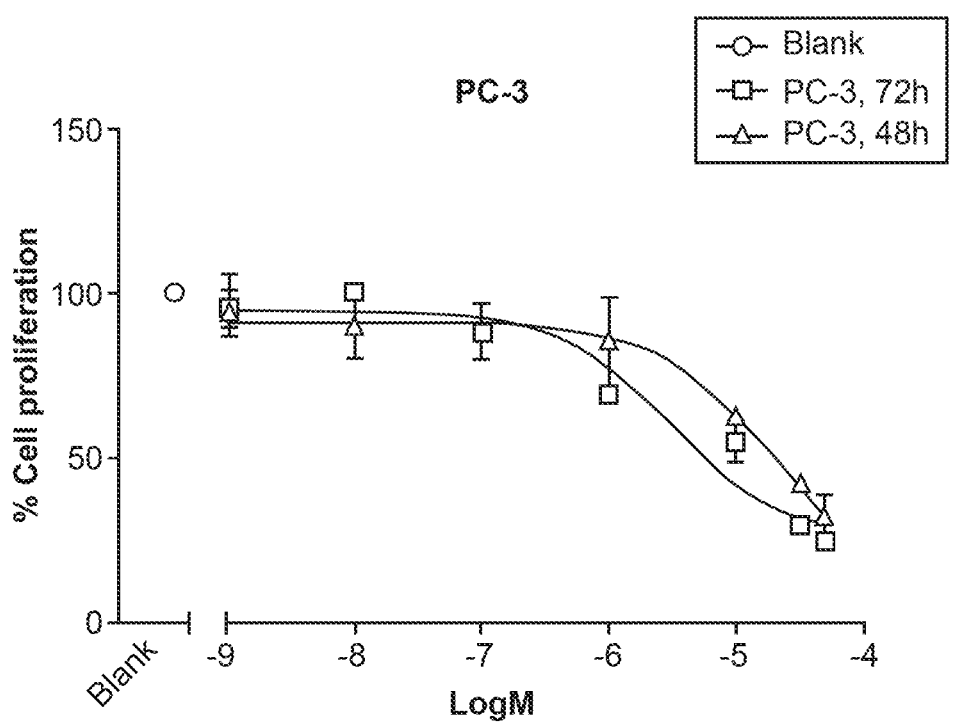
FIGS. 3A-3G plots cell proliferation data from prostate cancer cell lines (PC-3, LNCaP, DU145, 22Rv1, and C4-2), normal BPH-1 prostate cells, and non-prostate HEK cells treated with [D-Trp]CJ-15,208 after 48 h or 72 h, according to the working examples.
Figure 3B:
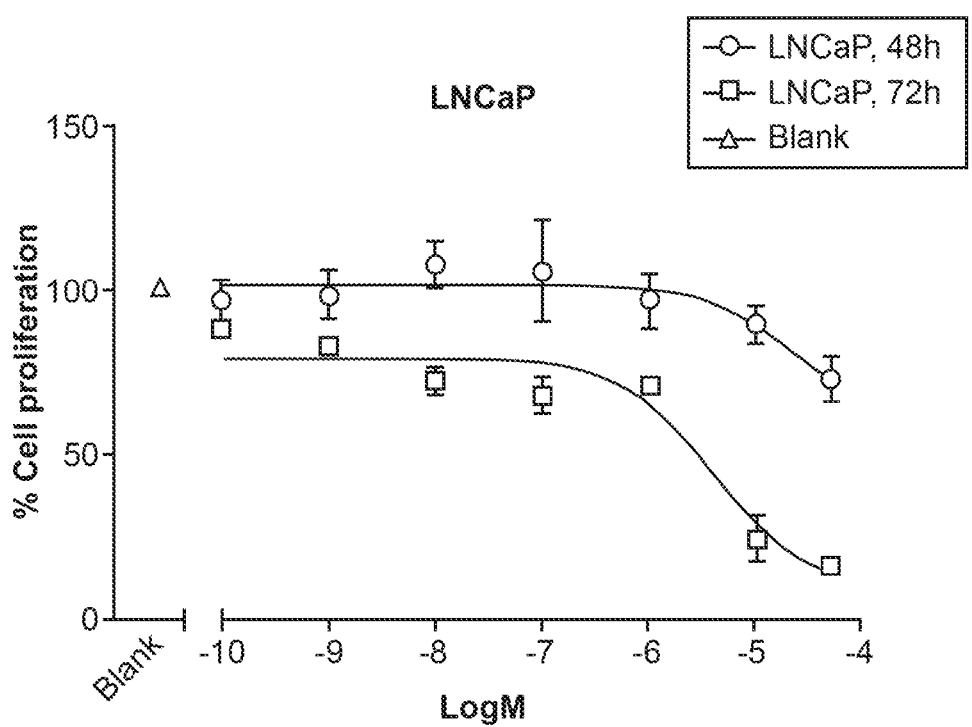
Figure 3C:
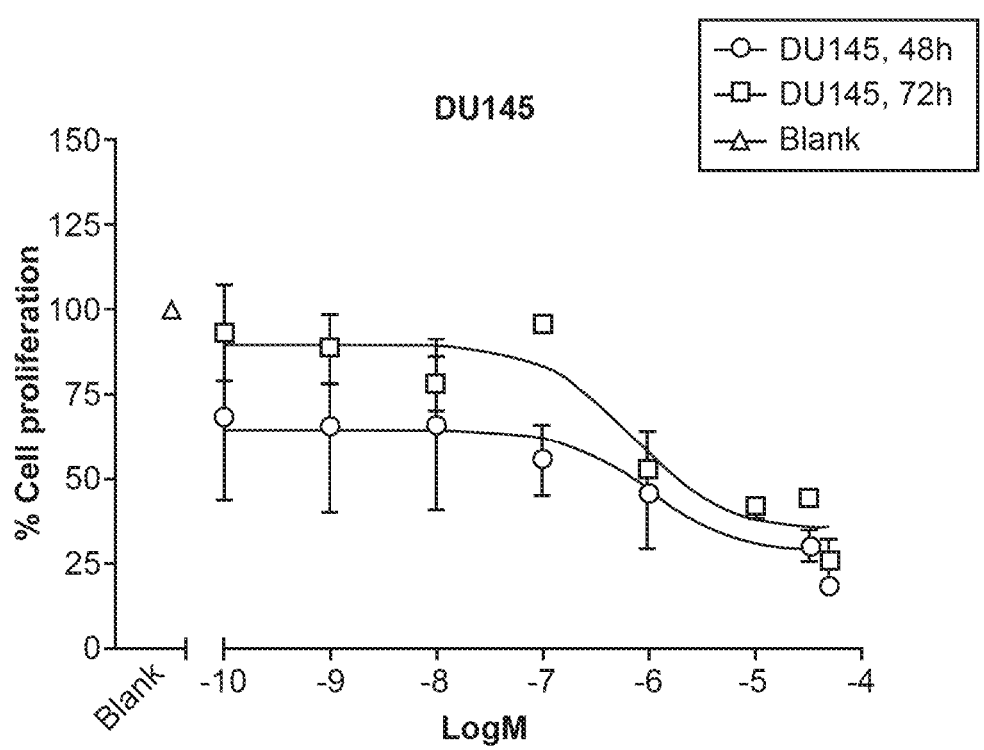
Figure 3D:
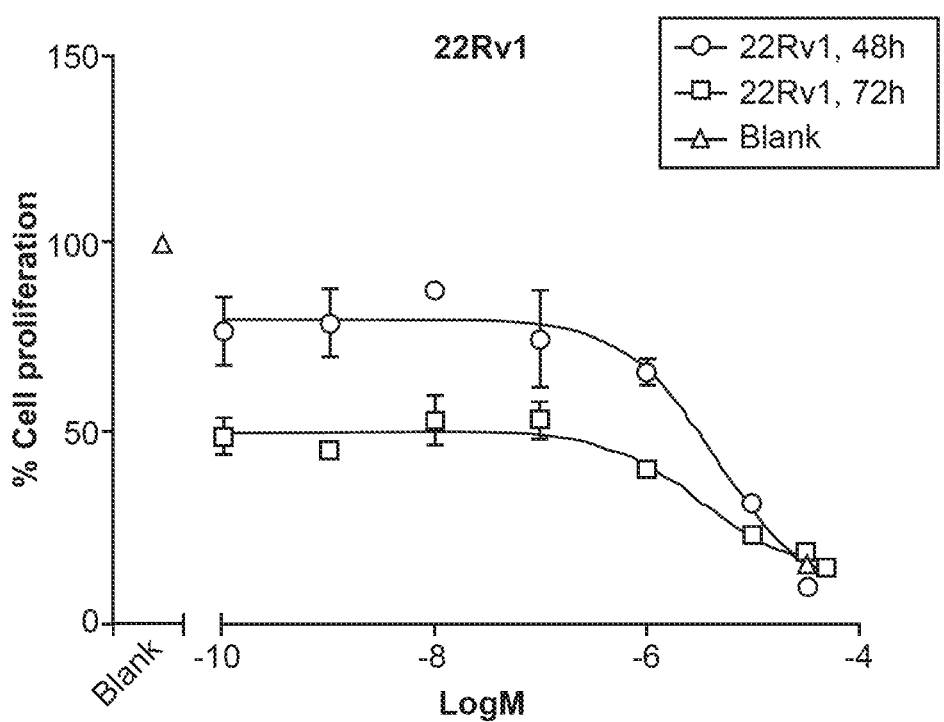
Figure 3E:
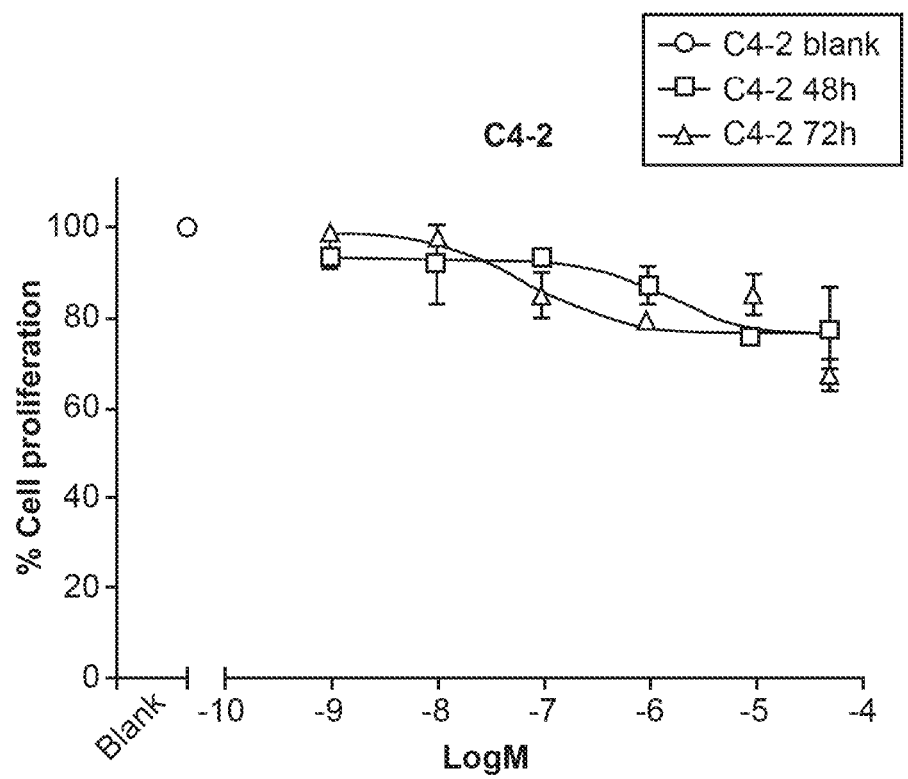
Figure 3F:
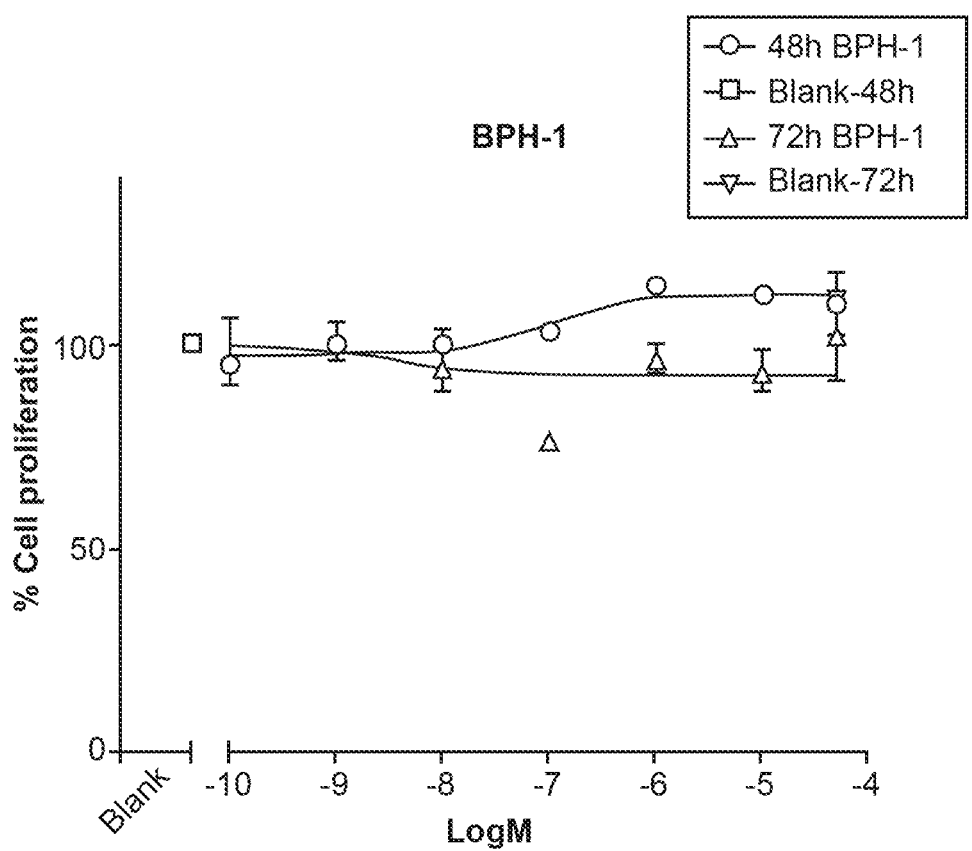
Figure 3G:
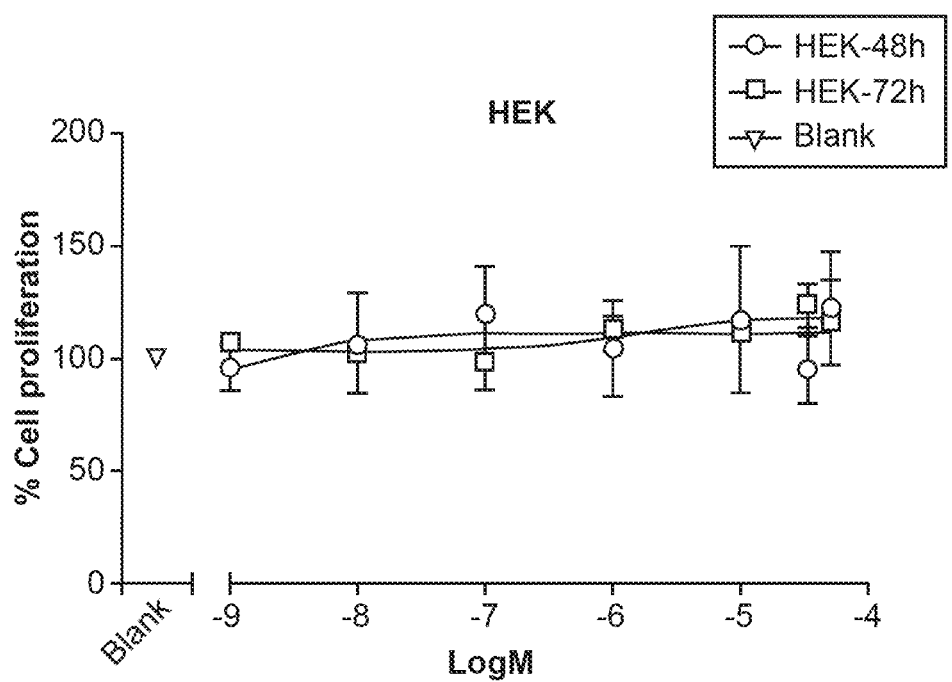
Figure 3H:
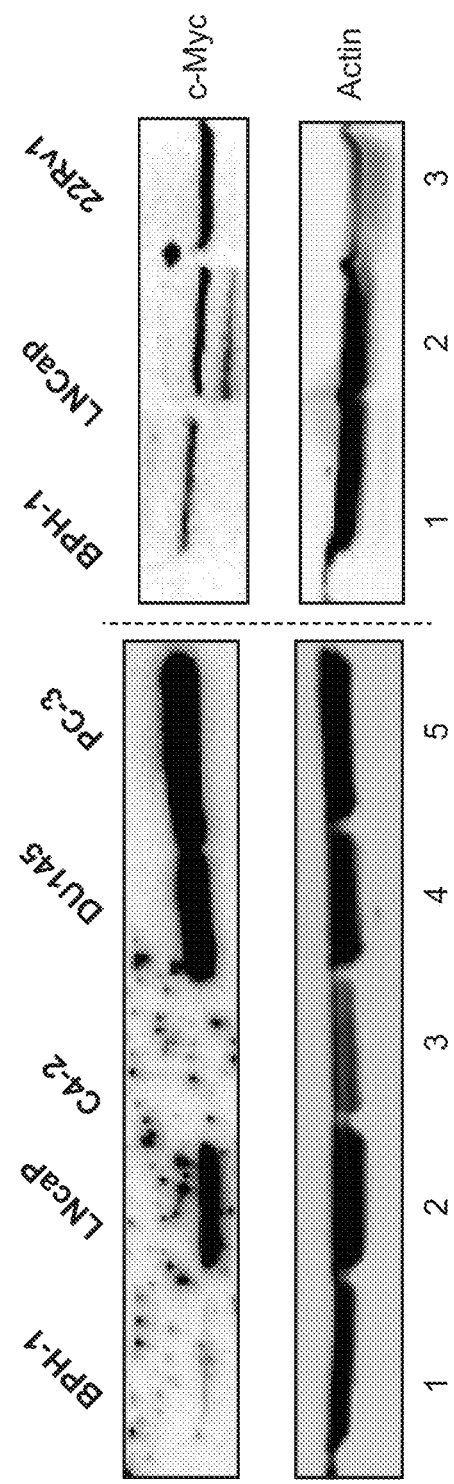
FIG. 3H illustrates the western blot analysis for c-Myc protein levels in PC-3, LNCaP, DU145, 22Rv1, C4-2, BPH-1, and HEK cells.
Figure 4A:
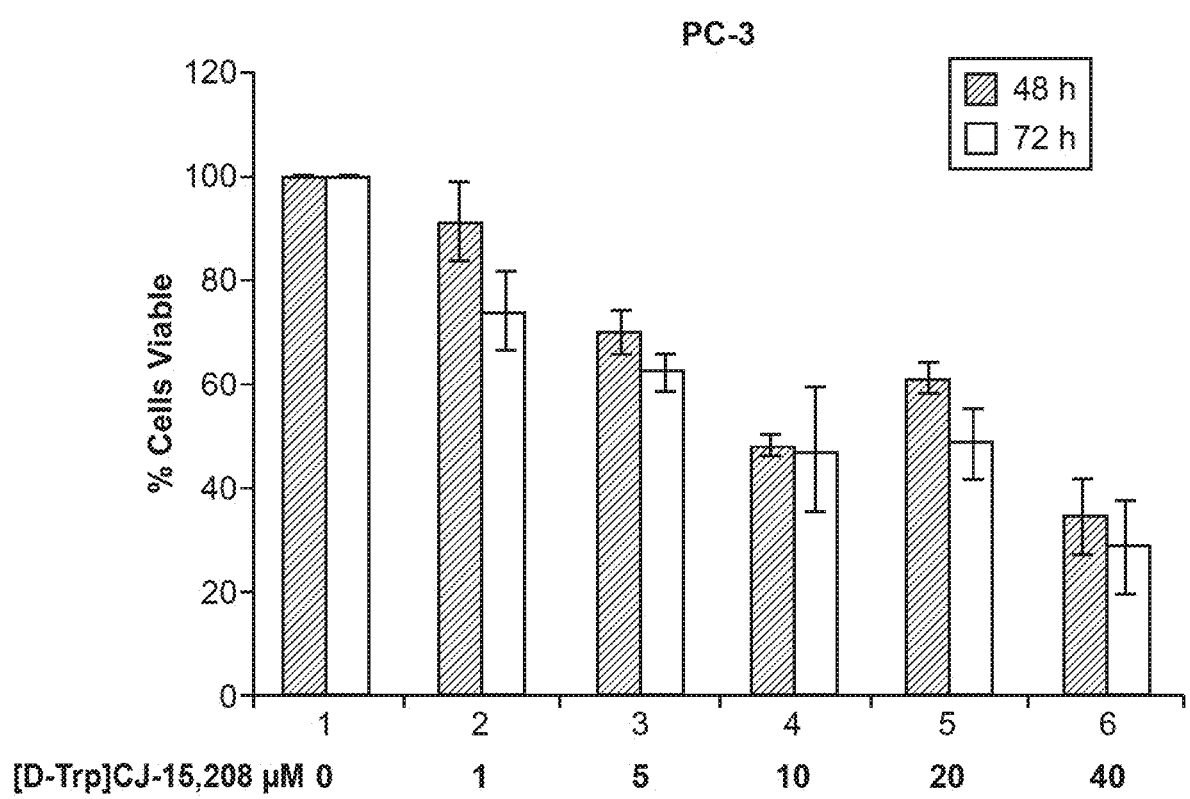
FIGS. 4A-4D provide graphs illustrating cytotoxicity in prostate cancer cells and normal prostate cells after treatment with [D-Trp]CJ-15,208 for 48 h or 72 h, where FIG. 4A provides the data from PC-3 cells, FIG. 4B the data from LNCaP cells, FIG. 4C the data from 22Rv1 cells, and FIG. 4D the data from BPH-1 cells, according to the working examples.
Figure 4B:
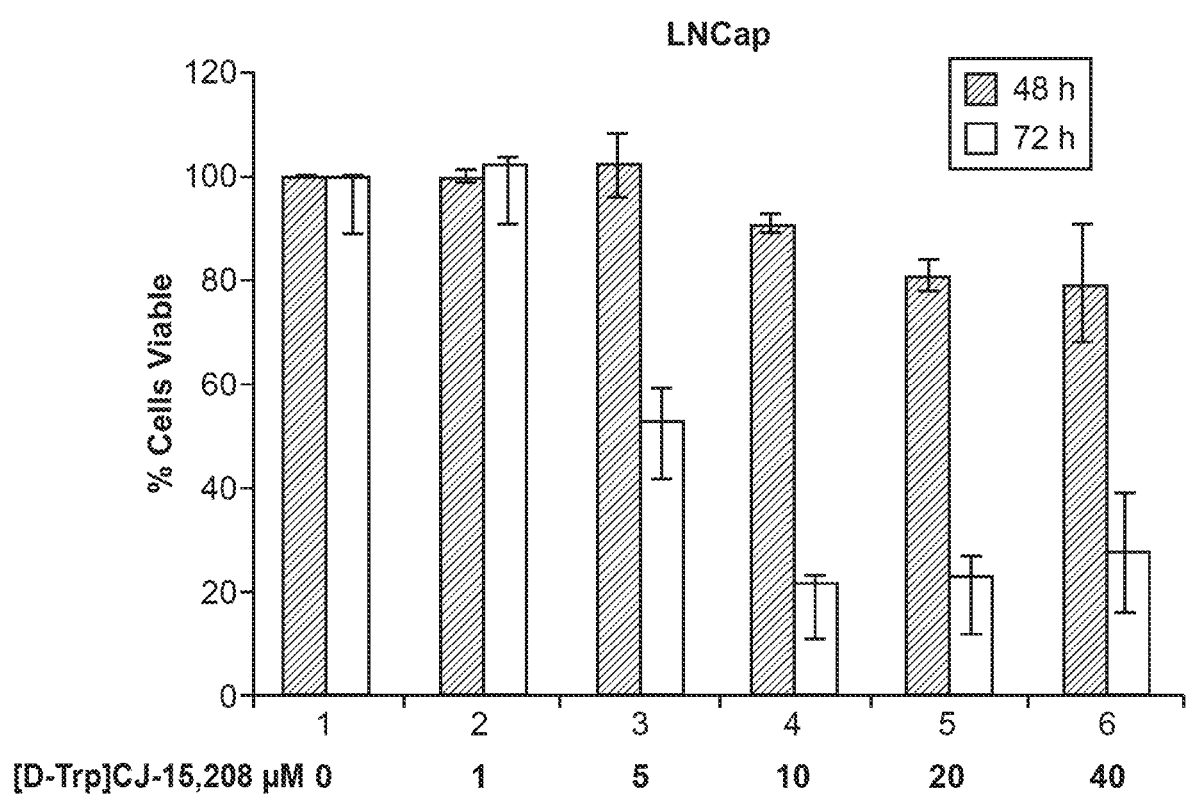
Figure 4C:
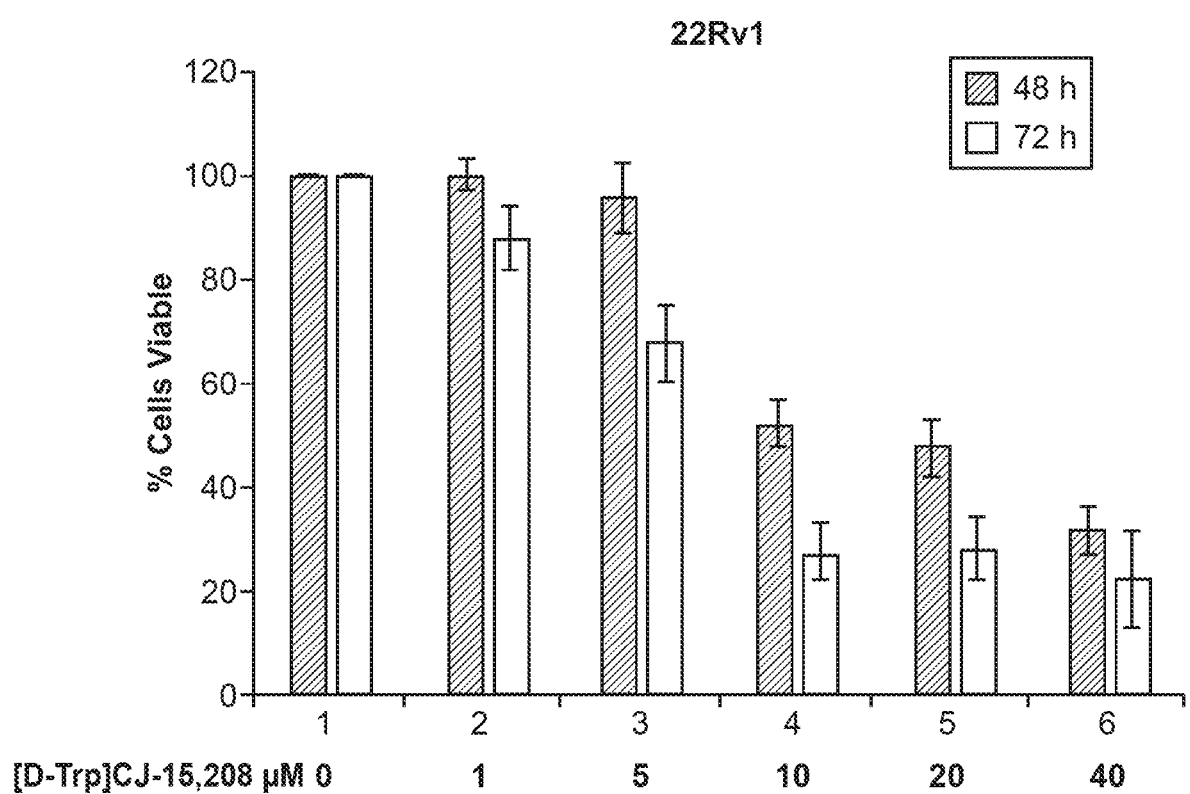
Figure 4D:
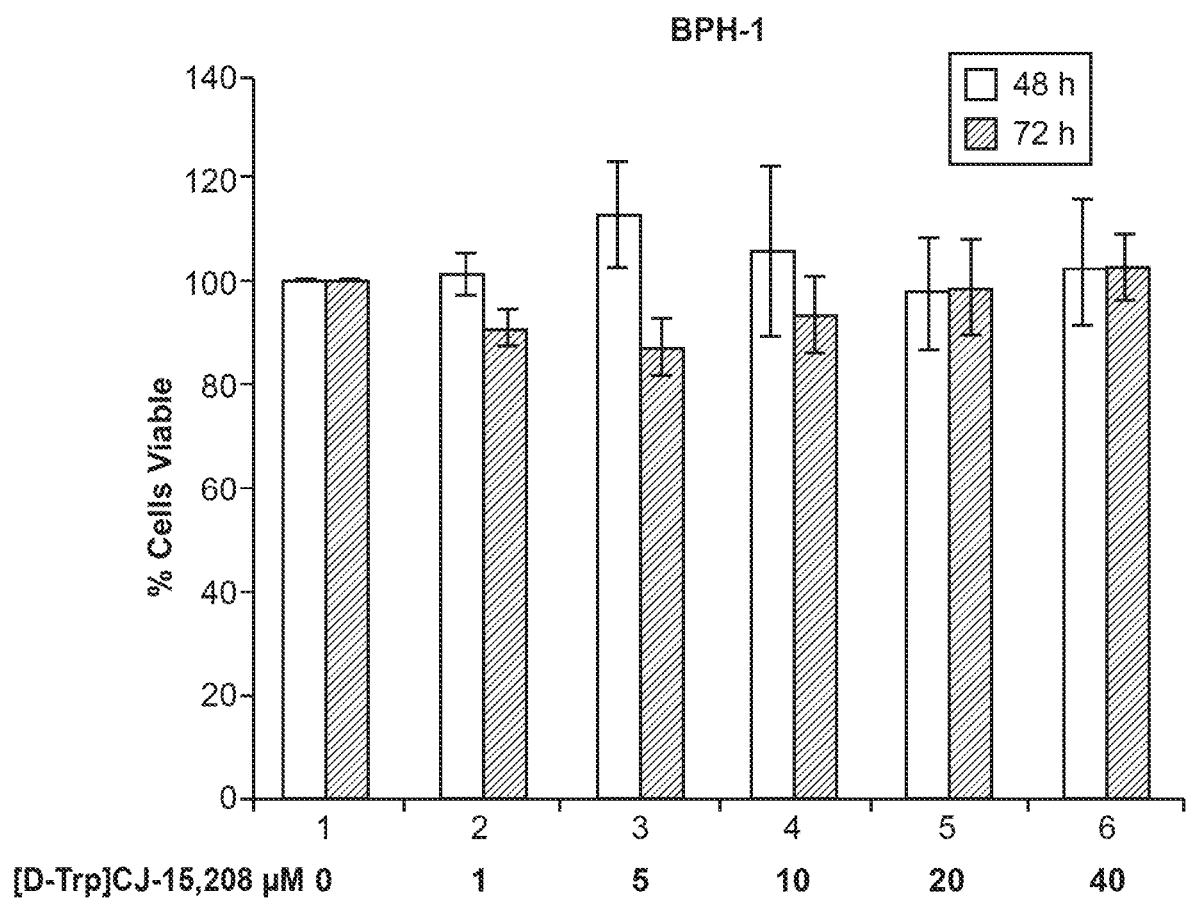

Cell proliferation (FIGS. 3A-3G) assays were performed using WST-1 (Roche) as described herein. [D-Trp]CJ-15,208 inhibited cell growth in most of the prostate cancer cell lines (Table 1), with $IC_{50}$ values of 3.0±1.0 μM in LNCaP cells following 72 h treatment, 1.2±0.2 μM in DU145 cells after 48 h treatment, and 8.8±4.0 μM in 22Rv1 cells after 48 h treatment. [D-Trp]CJ-15,208 had no effect on cell proliferation of C4-2 cells, a castration resistant prostate cancer (CRPC) cell line. No cytotoxicity was observed for [D-Trp]CJ-15,208 in BPH-1 cells or HEK cells (Table 1). The c-Myc protein levels in the different prostate cancer cell lines and normal cells (FIG. 3H) were consistent with [D-Trp]CJ-15,208's cytotoxicity. All of the prostate cancer cell lines except C4-2 cells expressed high levels of cellular c-Myc protein, while BPH-1 cells and C4-2 cells had low levels of c-Myc proteins.

Treatment of several prostate cancer cell lines with [D-Trp]CJ-15,208 resulted in decreased cell growth and cell death: i) the highly metastatic and androgen independent PC-3 cells, ii) mCRPC 22Rv1 cells, and iii) low metastatic, androgen dependent LNCaP cells, with $IC_{50}$ values ranging from 2 to 12 μM following 48-72 h treatment (FIGS. 3A-3H, Table 1). All of these cell lines where [D-Trp]CJ-15,208 decreased cell growth exhibited high c-Myc protein levels regardless of whether they were androgen dependent (LN-CaP) or independent metastatic (PC-3)/castration resistant (22Rv1) prostate cancer cells. Treatment with the peptide for 48 h decreased c-Myc protein levels in a concentration dependent manner in prostate cancer cells (FIGS. 2A-2D). Treatment with [D-Trp]CJ-15,208 did not prevent cell proliferation in C4-2 prostate cancer cells where c-Myc protein levels were not elevated, nor in normal cells (BPH-1 or HEK cells). Treatment with the peptide also did not alter cmyc mRNA levels. These results show that [D-Trp]CJ-15,208 inhibits cancer cell growth through its effects on c-Myc protein levels.

TABLE 1

[D-Trp]CJ-15,208 effect on cell growth.

| Cell line | Cancer cell line? | Androgen Responsive? | Androgen Receptor Overexpression? | 48 h *$IC_{50}$ (μM) | 72 h *$IC_{50}$ (μM) |
|---|---|---|---|---|---|
| [a]PC-3[46] | Yes | No, independent | Very low | 16.5 ± 0.7 | 2.0 ± 1.0 |
| [b]LNCaP[46] | Yes | Yes, dependent | Yes | >50 | 3.0 ± 1.1 |
| [c]DU145[46] | Yes | No, independent | Very low | 1.2 ± 0.2 | 0.7 ± 0.1 |
| [a,d]C4-2[46] | Yes | No, independent | Yes, mutated, truncated | No effect | No effect |
| [a,d]22Rv1[46] | Yes | No, independent | Yes, mutated, truncated | 8.8 ± 4.0 | 4.0 ± 0.8 |
| [e]BPH-1[46] | No | No | No, normal | No effect | No effect |
| [f]HEK | No | No | No | No effect | No effect |

*$IC_{50}$ values are the average ± S.E.M of triplicate measurement from two independent experiments;
[a]highly metastatic;
[b]low metastatic;
[c]moderately metastatic;
[d]castration resistant;
[e]normal prostate cells;
[f]non-prostate cells.

FIGS. 4A-D show that treatment of prostate cancer cells (PC-3, LNCaP, and 22Rv1) for 48 h and 72 h with [D-Trp]CJ-15,208 resulted in cell death using the Trypan blue assay as described herein. In contrast, no evidence of cell death was observed with BPH-1 cells after treatment with 1-40 μM of [D-Trp]CJ-15,208 for 48 h.

Figure 5A:
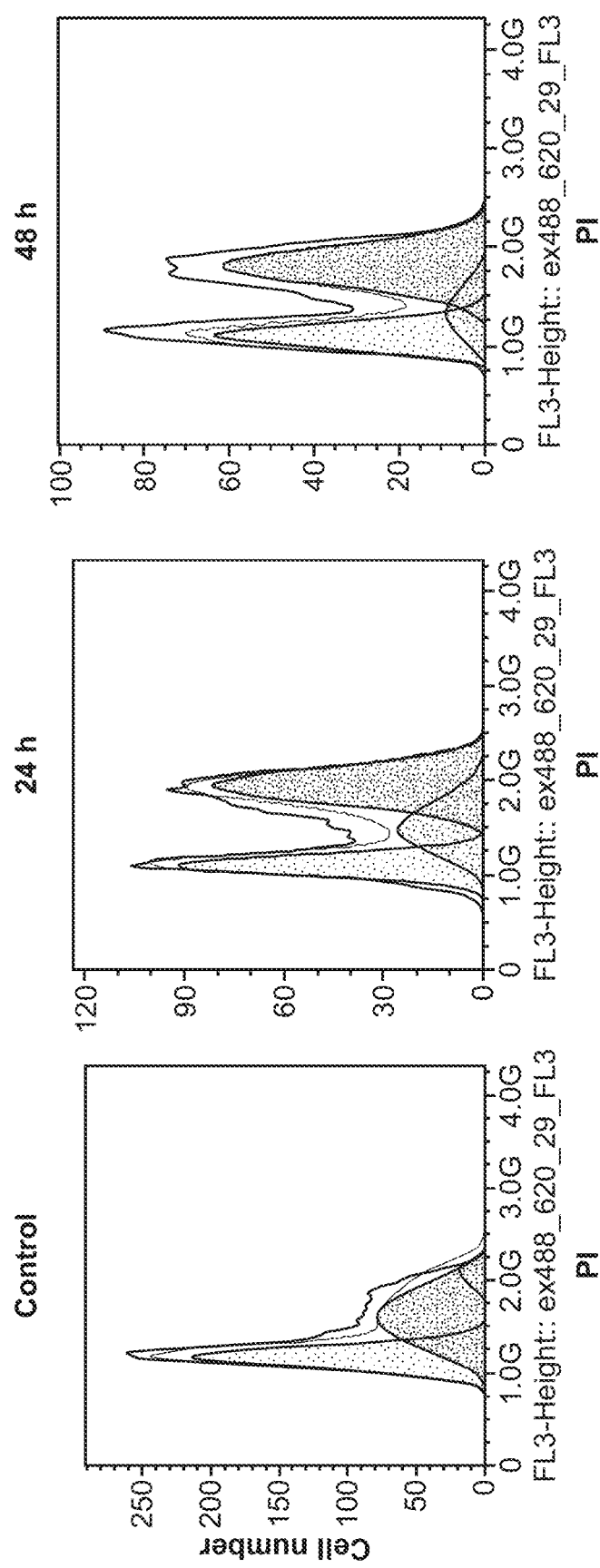
FIG. 5A illustrates the cell cycle phase distribution following 24 h and 48 h treatment of PC-3 cells with 10 µM [D-Trp]CJ-15,208, where FIG. 5B provides a graph illustrating the % cell population in each cell cycle phase, according to the working examples.
Figure 5B:
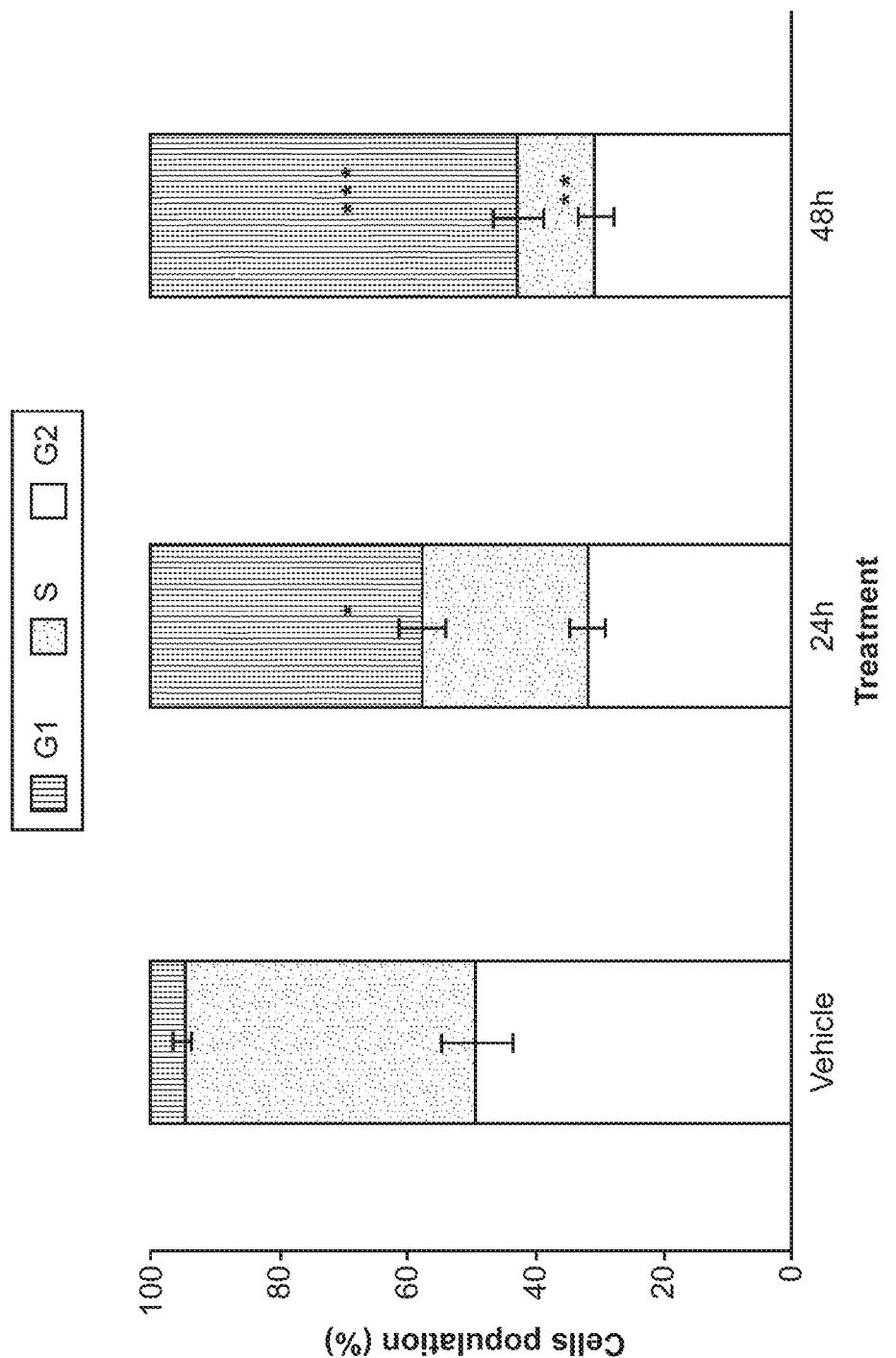

FIGS. 5A and 5B show the effect on cell cycle progression in PC-3 cells following treatment with [D-Trp]CJ-15,208 according to the present technology. Following treatment with 10 μM of [D-Trp]CJ-15,208 for 24 h or 48 h, a larger number of cells (at least 8-fold higher) accumulated in the G2 phase compared to vehicle treated control cells (5±1.5% for control, 42±4% following 24 h, and 58±4% following 48 h treatment). The mean cell population in G1 phase was 53±6% for control, 32±1% for 24 h, and 31±6% for 48 h treatment. The mean cell distribution in S phase was 45±4% for control, 26±4% following 24 h, and 12±0.6% following 48 h treatment.

[D-Trp]CJ-15,208 treatment induced apoptosis in PC-3 cells in a time-dependent manner and caused cell cycle arrest (FIGS. 5A and 5B). Increased early and late apoptosis were observed after 48 h treatment, but significant apoptosis induction was not found following 24 h treatment with [D-Trp]CJ-15,208. Cell cycle distribution is a complicated process, with c-Myc strictly controlling key cell cycle checkpoint proteins in the G1 to M phases including cyclins, CDKs, p21, and p53.[38] Several studies have demonstrated that cell cycle arrest by c-Myc suppression can occur via two mechanisms: i) uncontrolled expression of c-Myc-dependent checkpoint genes, such as CDKs or CDKIs (p21), or ii) changes in gene expression in specific cellular metabolic pathways that are directly regulated by c-Myc.[41-43] Treatment of PC-3 cells with [D-Trp]CJ-15,208 for 24 h or 48 h resulted in cell cycle arrest in the G2 phase, preventing cancer cells from entering mitosis and cell division. These results indicate that [D-Trp]CJ-15,208 significantly induces growth arrest at the G2 phase in cell cycle progression in PC-3 cells (FIG. 5B).

Figure 6A:
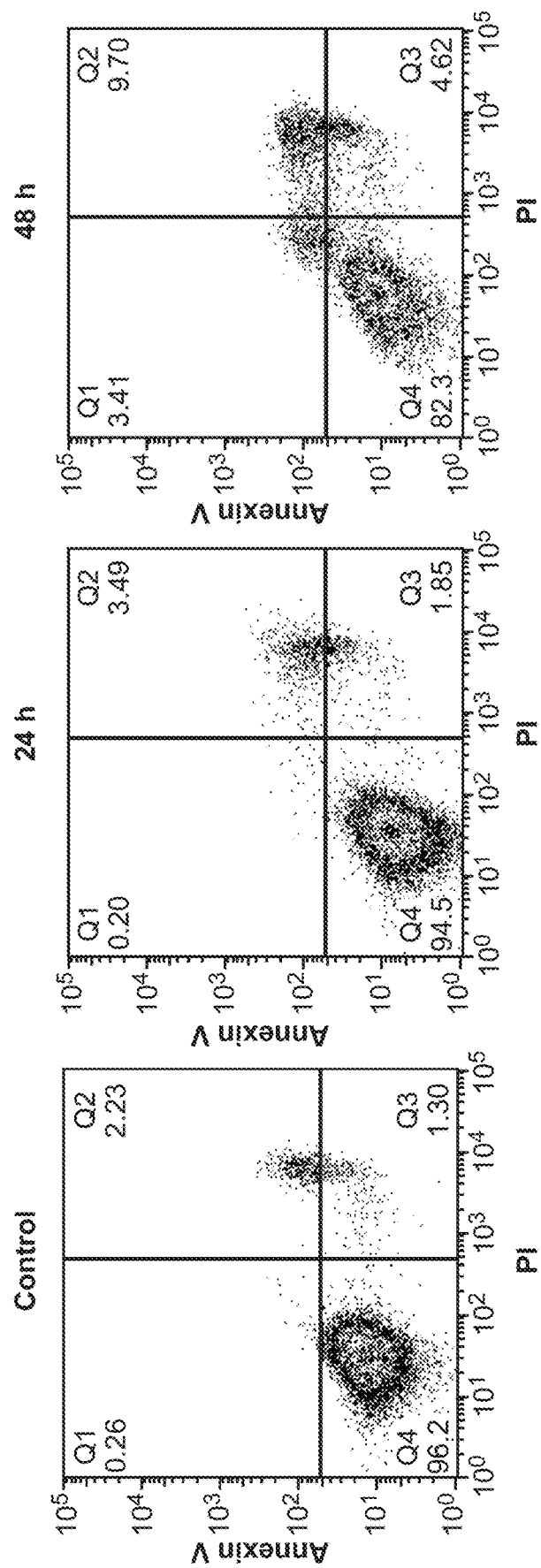
FIG. 6A illustrates the flow cytometry analysis showing the extent of apoptosis for PC-3 following treatment with [D-Trp]CJ-15,208 for 48 h, and FIG. 6B graphs the % cell population in early and late apoptosis, according to the working examples.
Figure 6B:
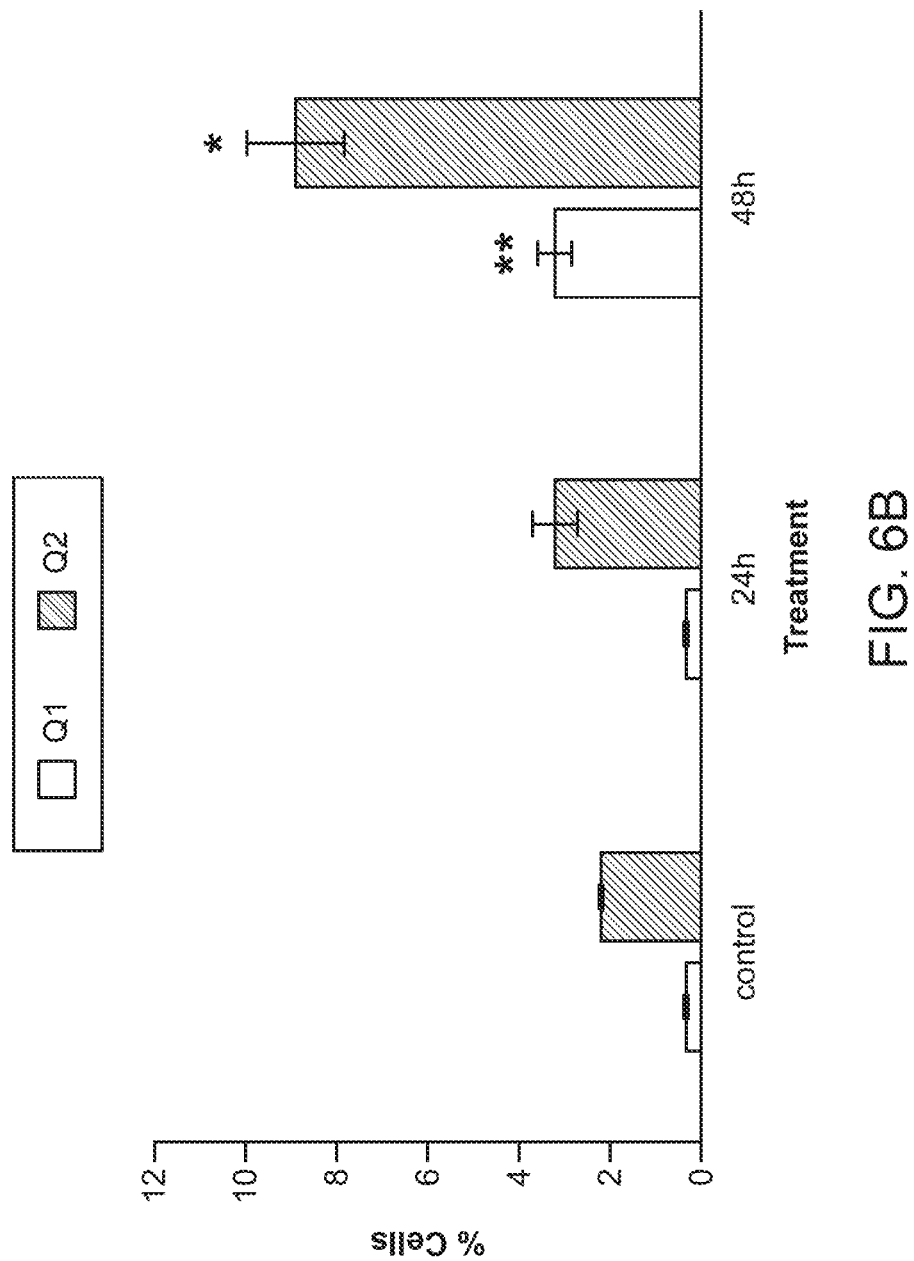

FIGS. 6A and 6B demonstrate induction of apoptosis in PC-3 cells. In FIG. 6A, the upper left quadrant (Q1) showed the presence of early apoptotic cells which were positively stained by annexin V but not stained by PI, the upper right quadrant (Q2) showed the late apoptotic cells which were positively stained by both PI and annexin V, the lower right quadrant (Q3) showed the dead cells that were positively stained only by PI but not by annexin V, and the lower left quadrant (Q4) showed the viable cells which were not stained by either PI or annexin V. As shown in FIG. 6B, following 48 h treatment with 10 μM of [D-Trp]CJ-15,208, the number of cells in early and late apoptosis increased by 10- and 3-fold, respectively, compared to vehicle treated control cells. No significant change in the number of cells was observed in early or late apoptosis following 24 h treatment with 10 μM of [D-Trp]CJ-15,208 (FIG. 6B).

Figure 7A:
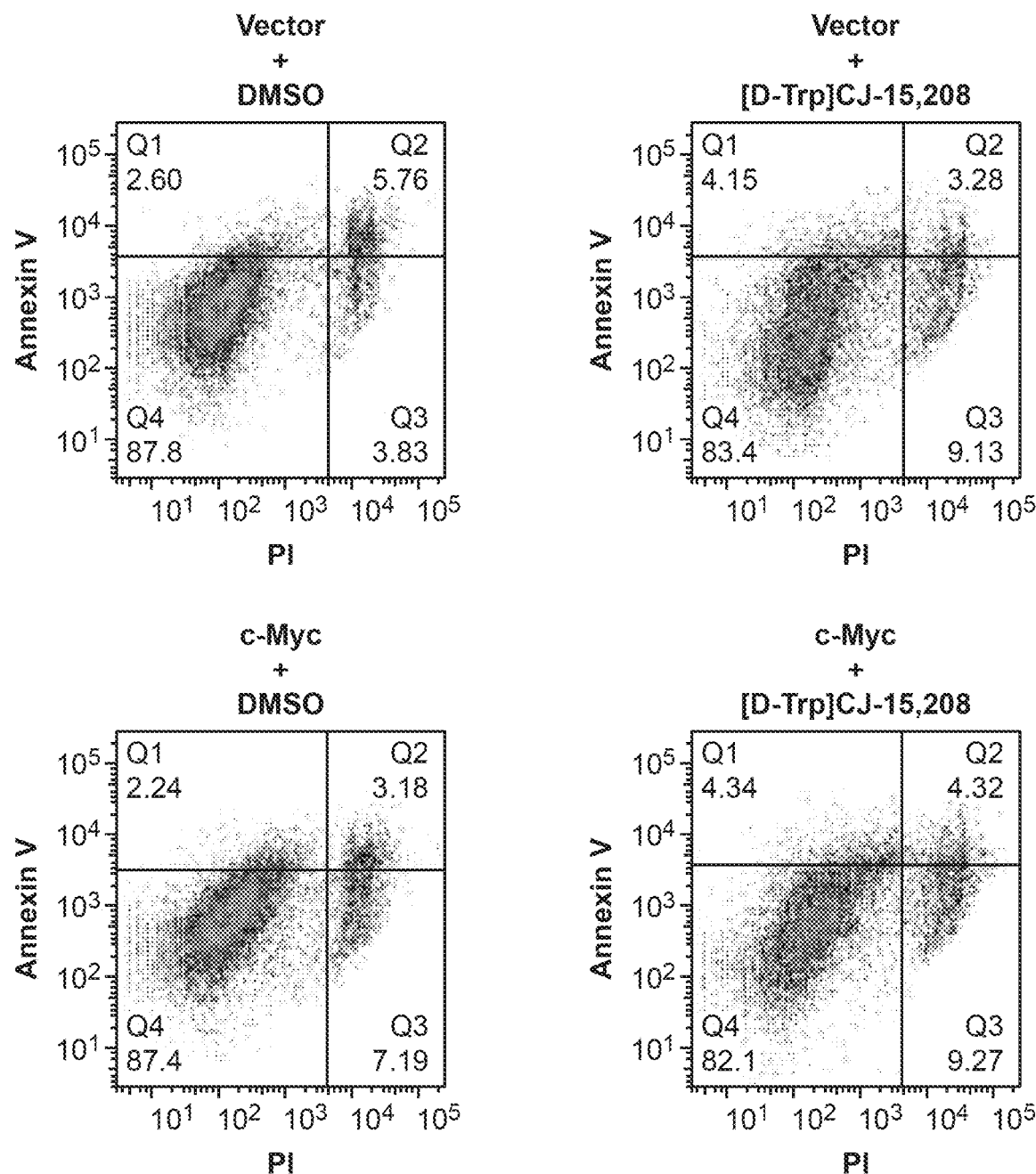
FIG. 7A illustrates the flow cytometry analysis showing the extent of apoptosis of nontargeting siRNA or c-Myc siRINA treated PC-3 cells following treatment with [D-Trp]CJ-15,208 for 48 h.
Figure 7B:
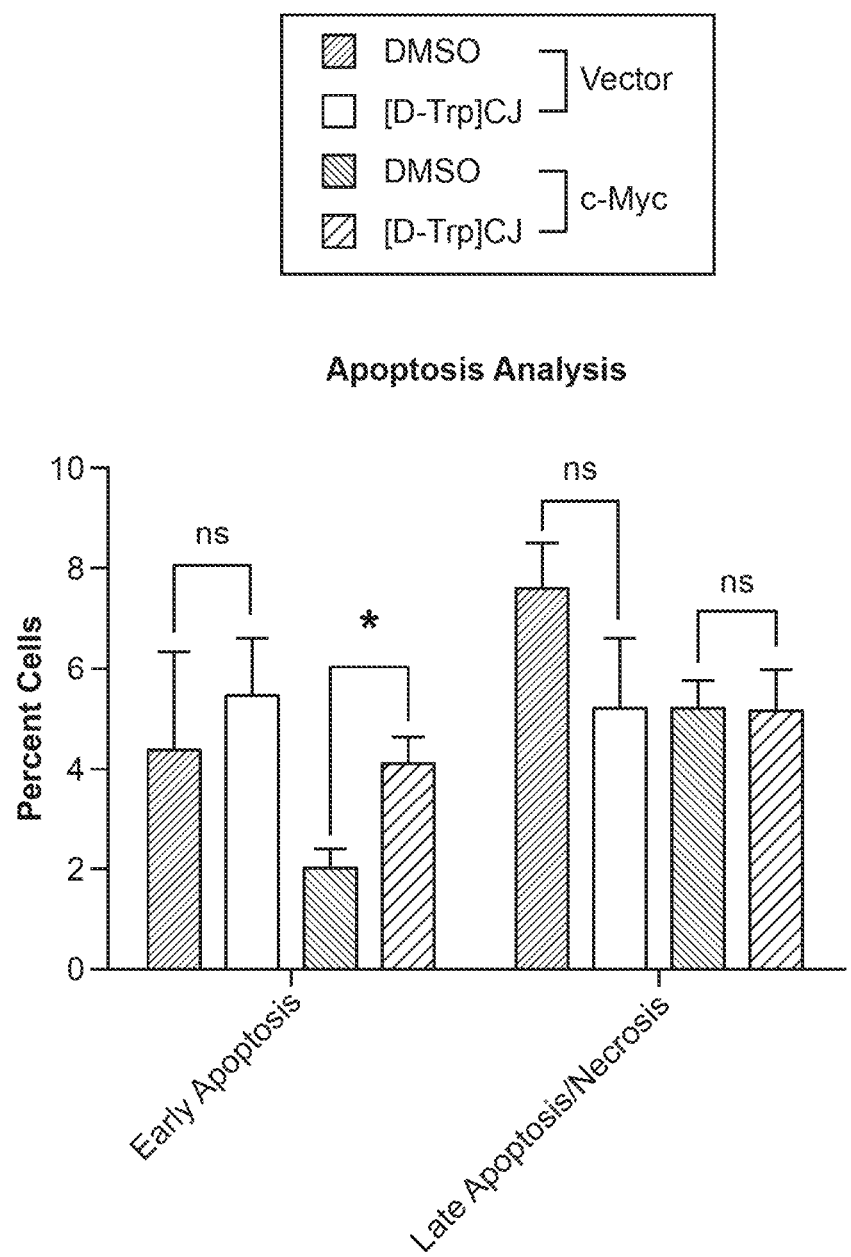
FIG. 7B illustrates the % cell population in early and late apoptosis in PC-3 cells, and FIG. 7C provides the western blot analysis showing c-Myc knockdown by the c-Myc siRNA, according to the working examples.
Figure 7C:
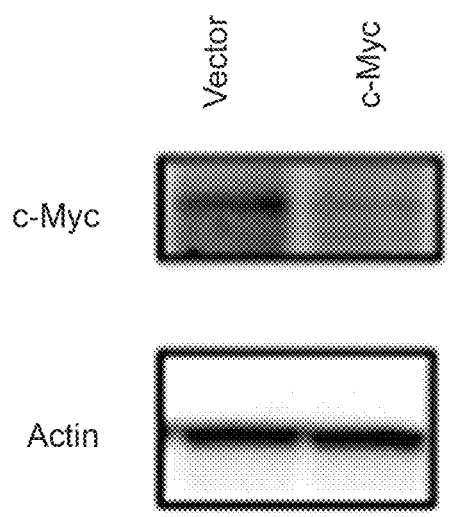

Knockdown and overexpression of c-Myc experiments were performed to show the c-Myc downregulation effects of [D-Trp]CJ-15,208. FIG. 7A shows the knockdown experiments for PC-3 cells transfected with either siRNA against c-Myc or a nontargeting siRNA and subsequently treated with 10 μM [D-Trp]CJ-15,208 for 48 h. The cells were analyzed for apoptosis. FIG. 7B shows that treatment with [D-Trp]CJ-15,208 significantly increased early apoptosis in cells transfected with nontargeting siRNA, but did not significantly affect the percent of cells transfected with the siRNA against c-Myc that underwent early apoptosis. FIG. 7C shows the Western blot analysis for the knockdown of c-Myc in the cells transfected with siRNA against c-Myc. Thus, the data illustrates that PC-3 cells in which c-Myc is down regulated no longer exhibit an increase in early apoptosis upon treatment with the peptide.

Figure 8A:
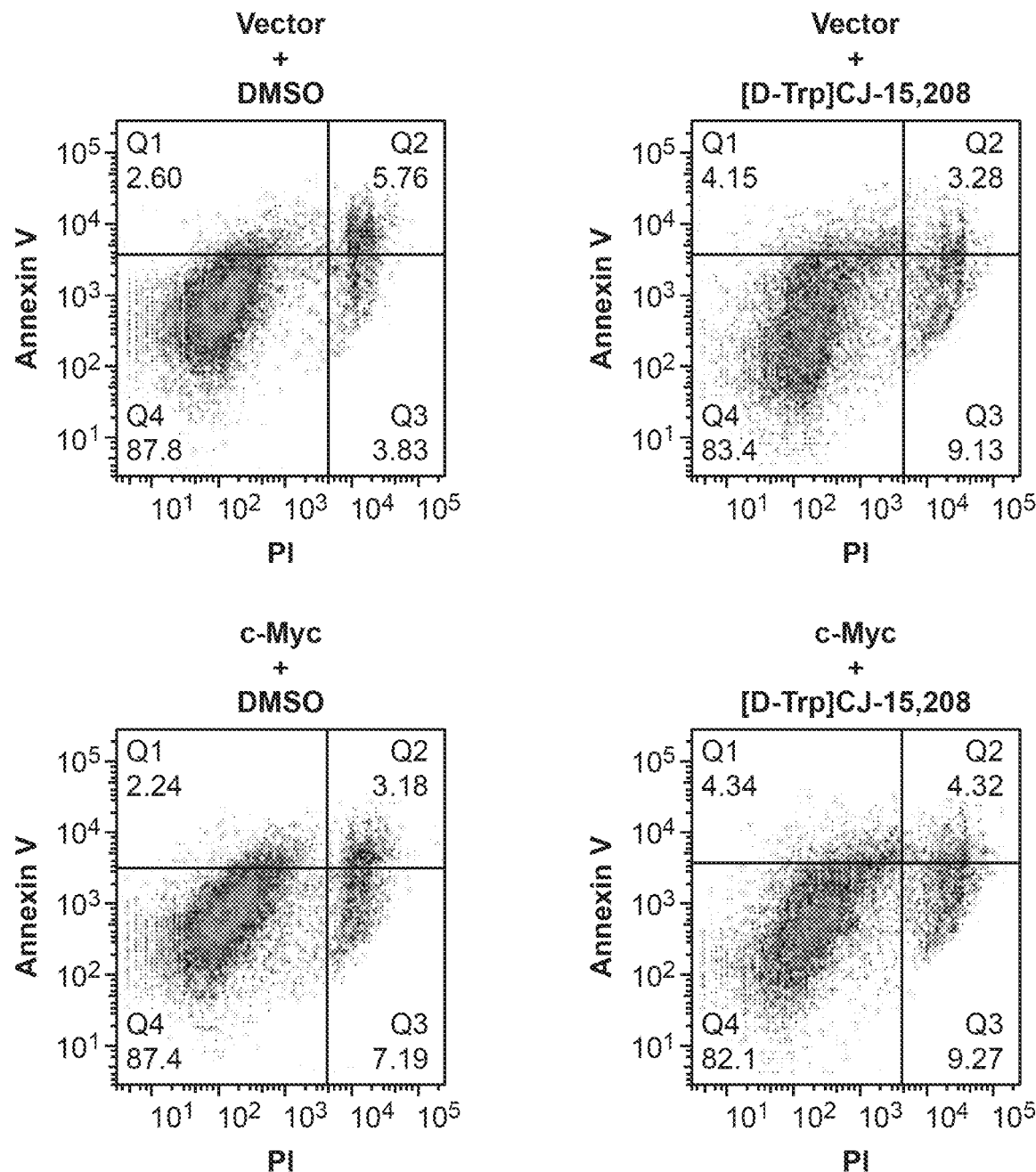
FIG. 8A illustrates the flow cytometry analysis to show extent of apoptosis of vector control plasmid or HA-HA-c-Myc plasmid containing HEK-293 cells following treatment with [D-Trp]CJ-15,208 for 48 h, FIG. 8B graphs the % cell population in early and late apoptosis.
Figure 8B:
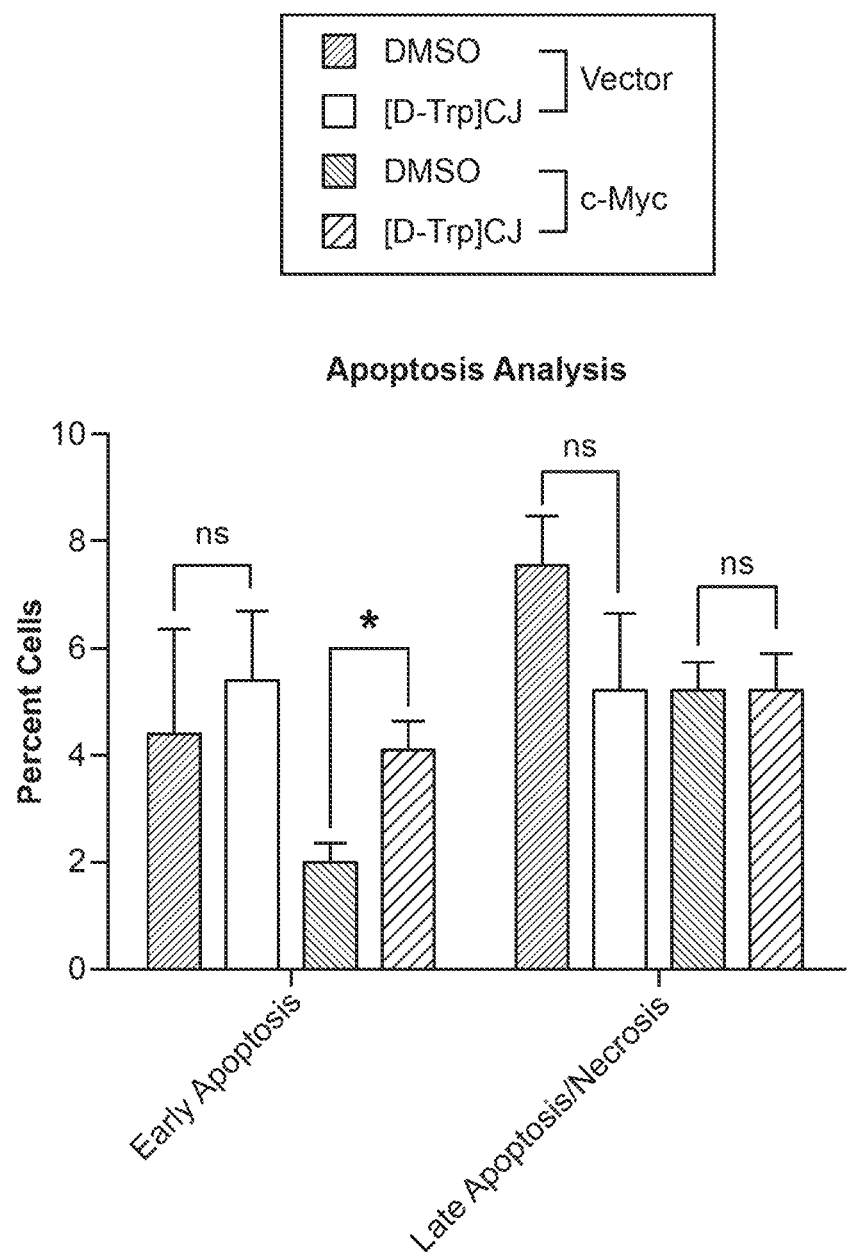
FIG. 8C illustrates the western blot analysis showing c-Myc transfection in HA-HA-c-Myc plasmid containing HEK-293 cells.
Figure 8C:
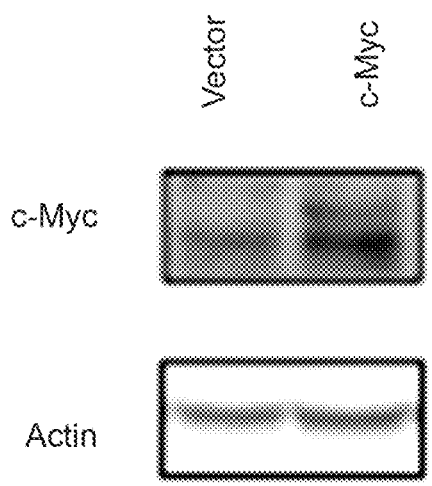

HEK-293 cells transfected with either a pcDNA containing an HA-tagged human c-Myc insert to overexpress the protein or a vector control were also treated with 10 μM [D-Trp]CJ-15,208 for 48 h and the cells were analyzed for apoptosis. FIG. 8B shows that cells that overexpressed c-Myc and treated with [D-Trp]CJ-15,208 showed a significant increase in early apotosis, consistent with what was observed in PC-3 cells. However, no significant difference was seen in cells transfected with the empty vector. FIG. 8C provides the Western blot analysis showing the overexpression of c-Myc in the cells transfected with the c-Myc containing plasmid. In complimentary gain of function experiments, HEK-cells overexpressing c-Myc became sensitive to treatment with [D-Trp]CJ-15,208, exhibiting a significant increase in early apoptosis following treatment with the peptide (FIGS. 8A-8C).

Figure 9A:
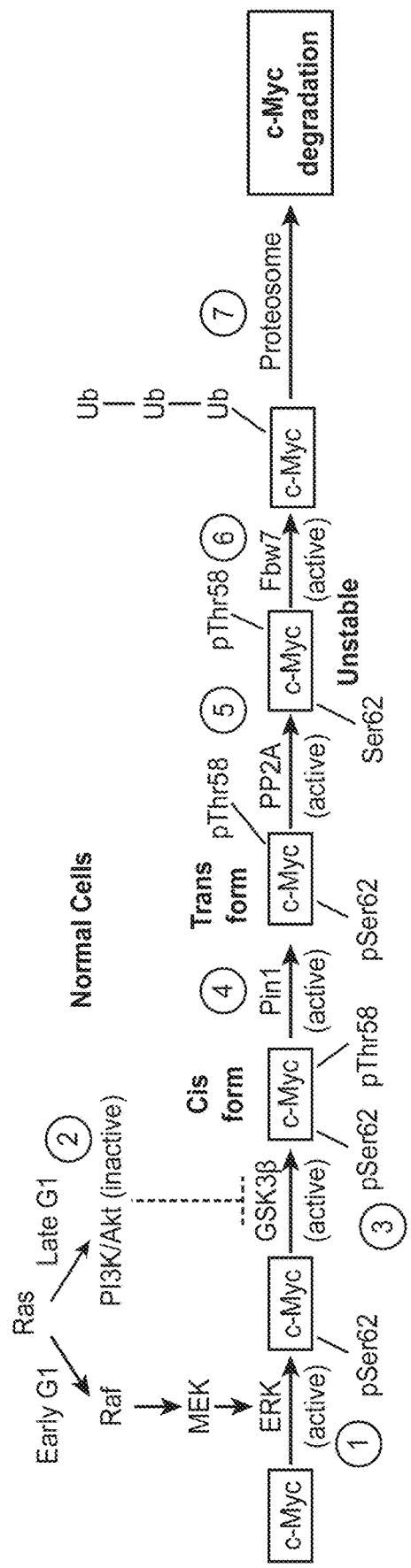
FIGS. 9A and 9B illustrate the c-Myc phosphorylation and degradation pathway in normal cells (FIG. 9A) and cancer cells (FIG. 9B).
Figure 9B:
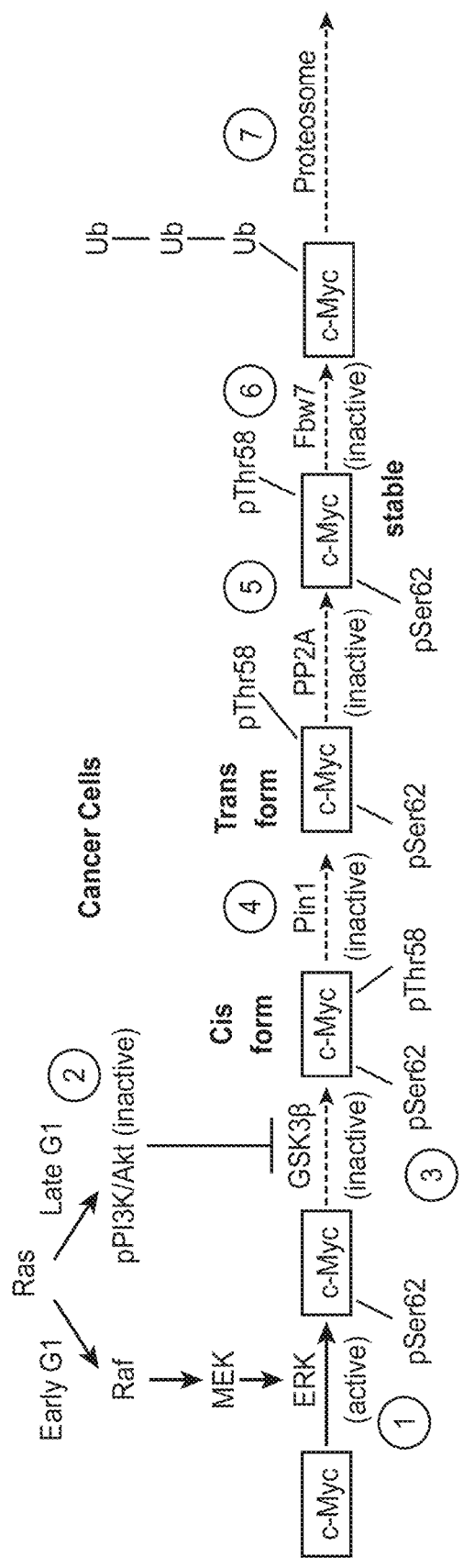

The stability of cellular c-Myc protein was determined by the tight regulation of its phosphorylation state.[11,13,33] c-Myc protein degradation is important to maintain normal cellular functions, whereas high levels of c-Myc protein have been found in various cancer cells including prostate cancer.[13, 16] The schematic diagrams in FIGS. 9A and 9B illustrate the pathway that determines c-Myc stability in normal (FIG. 9A) vs. cancer cells (FIG. 9B). A series of key enzymes, mainly Erk, PI3K/Akt, and PP2A, are involved in regulating c-Myc phosphorylation and its degradation via this pathway.

The phosphorylation state of c-Myc plays a major role in determining c-Myc stability and accumulation in cells. Under normal cellular conditions (FIG. 9A), Ras activation in the early G1 phase of the cell cycle triggers c-Myc phosphorylation and degradation through an orchestrated cascade of enzymatic reactions. In contrast to normal cells, Ras activates both Erk and Akt by phosphorylation in the late and early G1 phase in malignant cells, enhancing c-Myc stability (FIG. 9B). p-Erk phosphorylates c-Myc on Ser62 and p-Akt inhibits GSK-3β phosphorylation of c-Myc on Thr58. These phosphorylation events prevent the rest of the steps in the c-Myc degradation pathway, increasing c-Myc stability in cells[11, 13] (FIG. 9B).

Figure 10A:
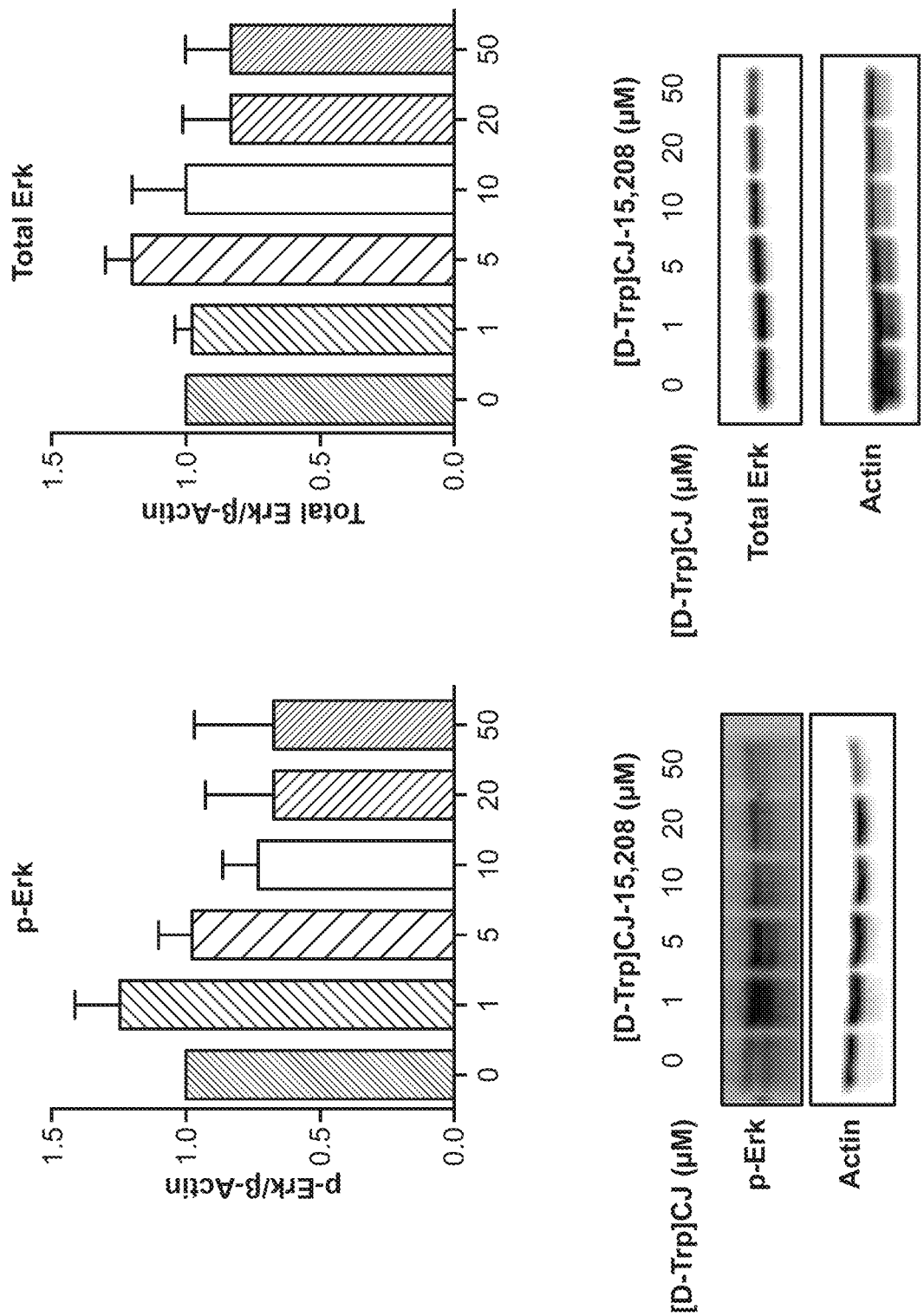
FIGS. 10A-10C graph and provide western blot analysis illustrating key protein levels (Erk, Akt, and PP2A) following treatment with [D-Trp]CJ-15,208 after 48 h, where FIG.
Figure 10B:
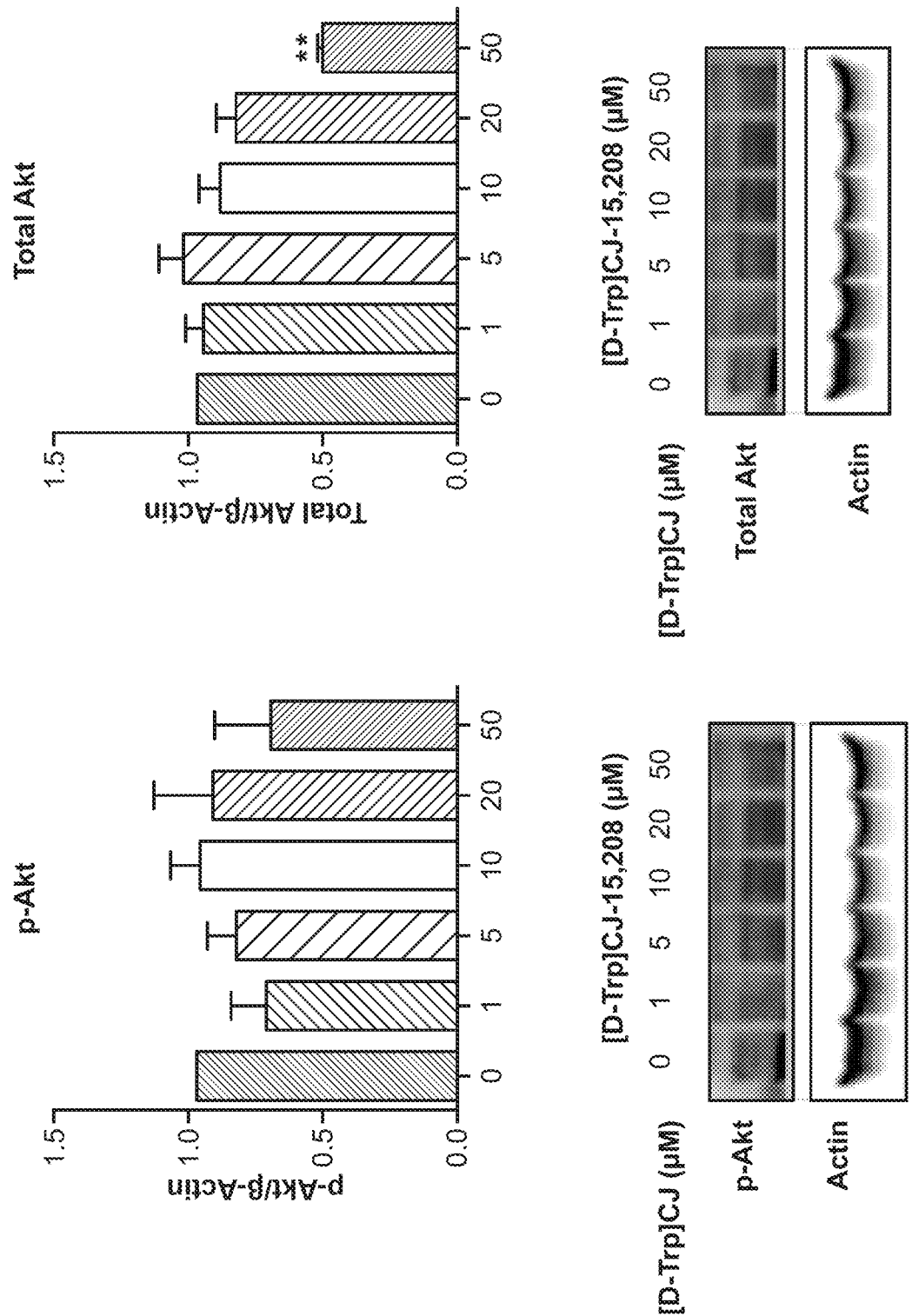
Figure 10C:
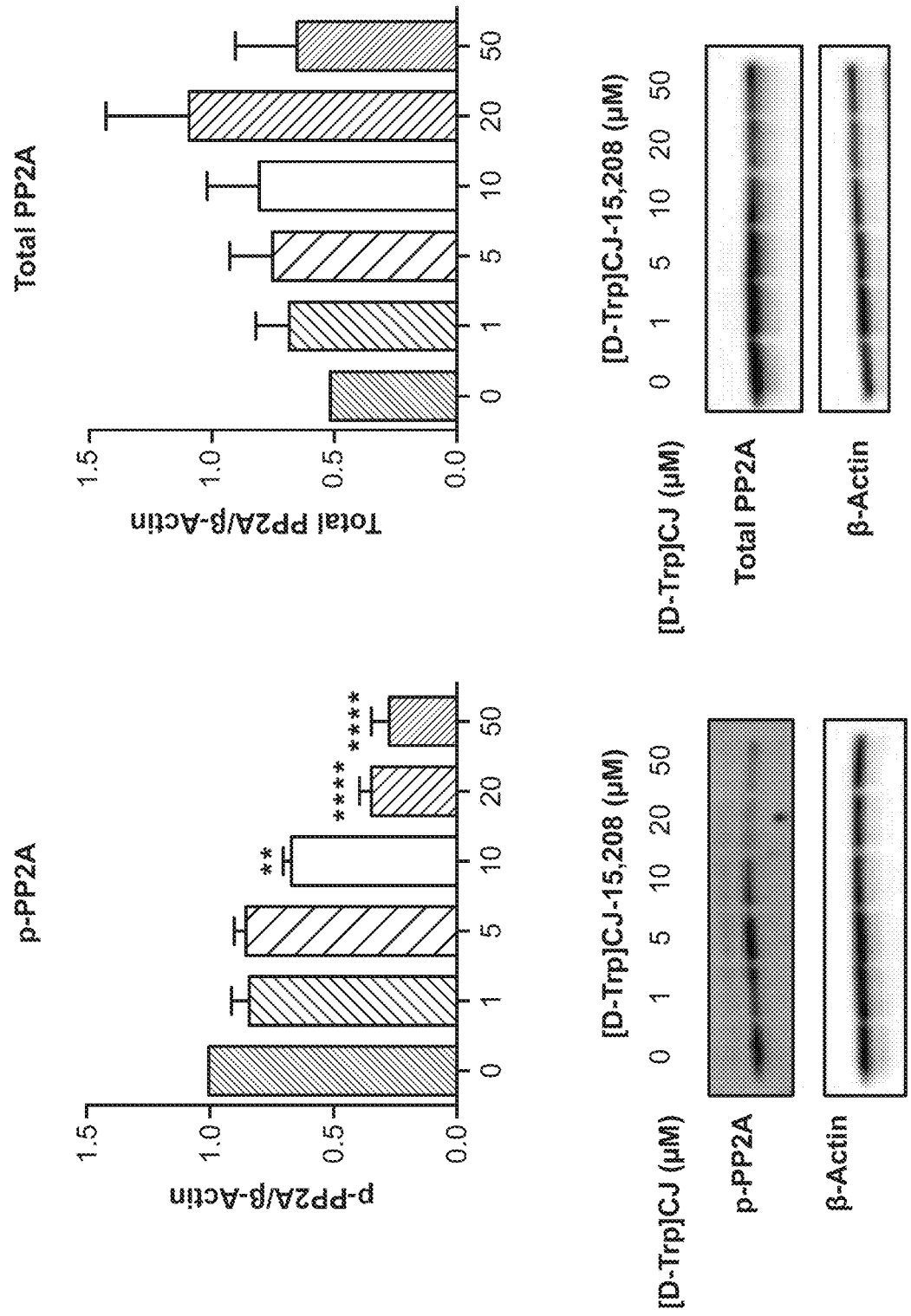
Figure 10D:
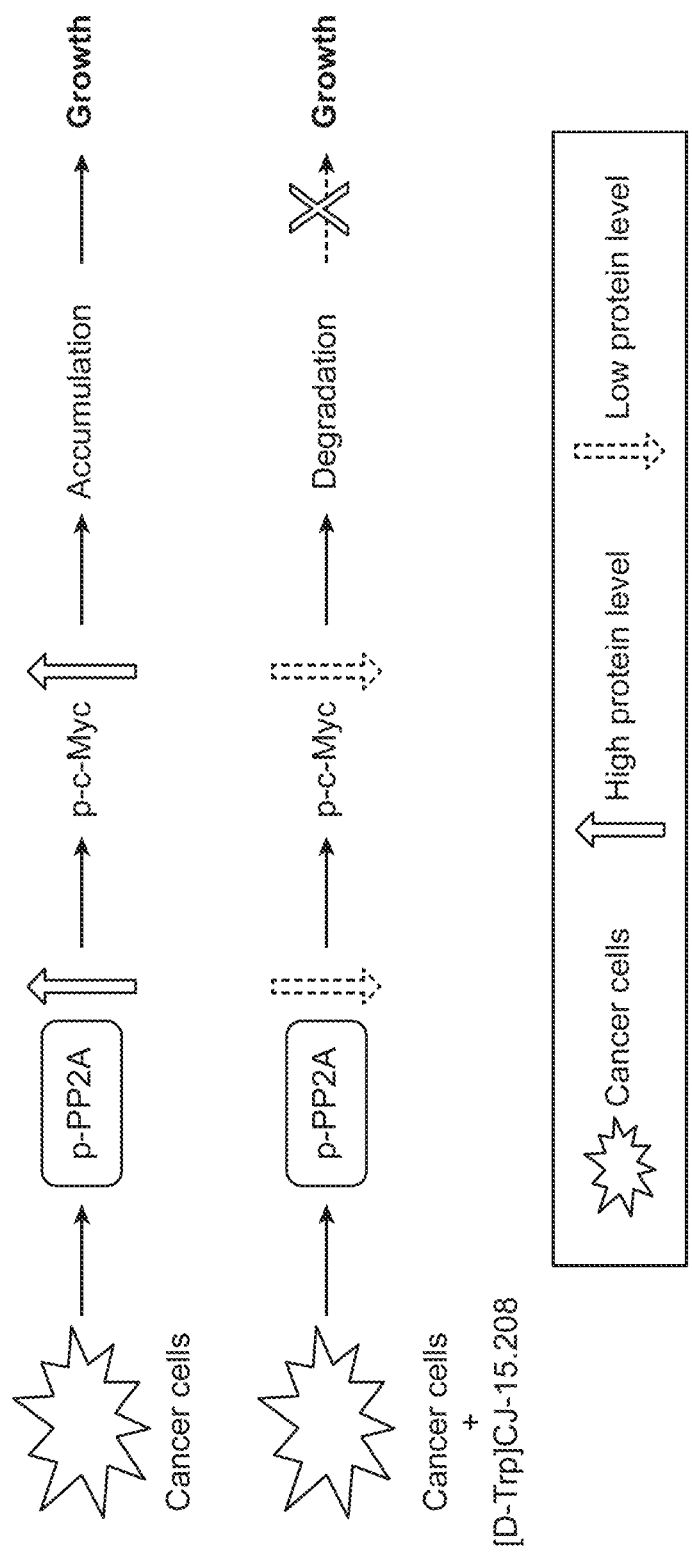
FIG. 10D illustrates the effects of treatment of PC-3 cells with [D-Trp]CJ-15,208.
Figure 11:
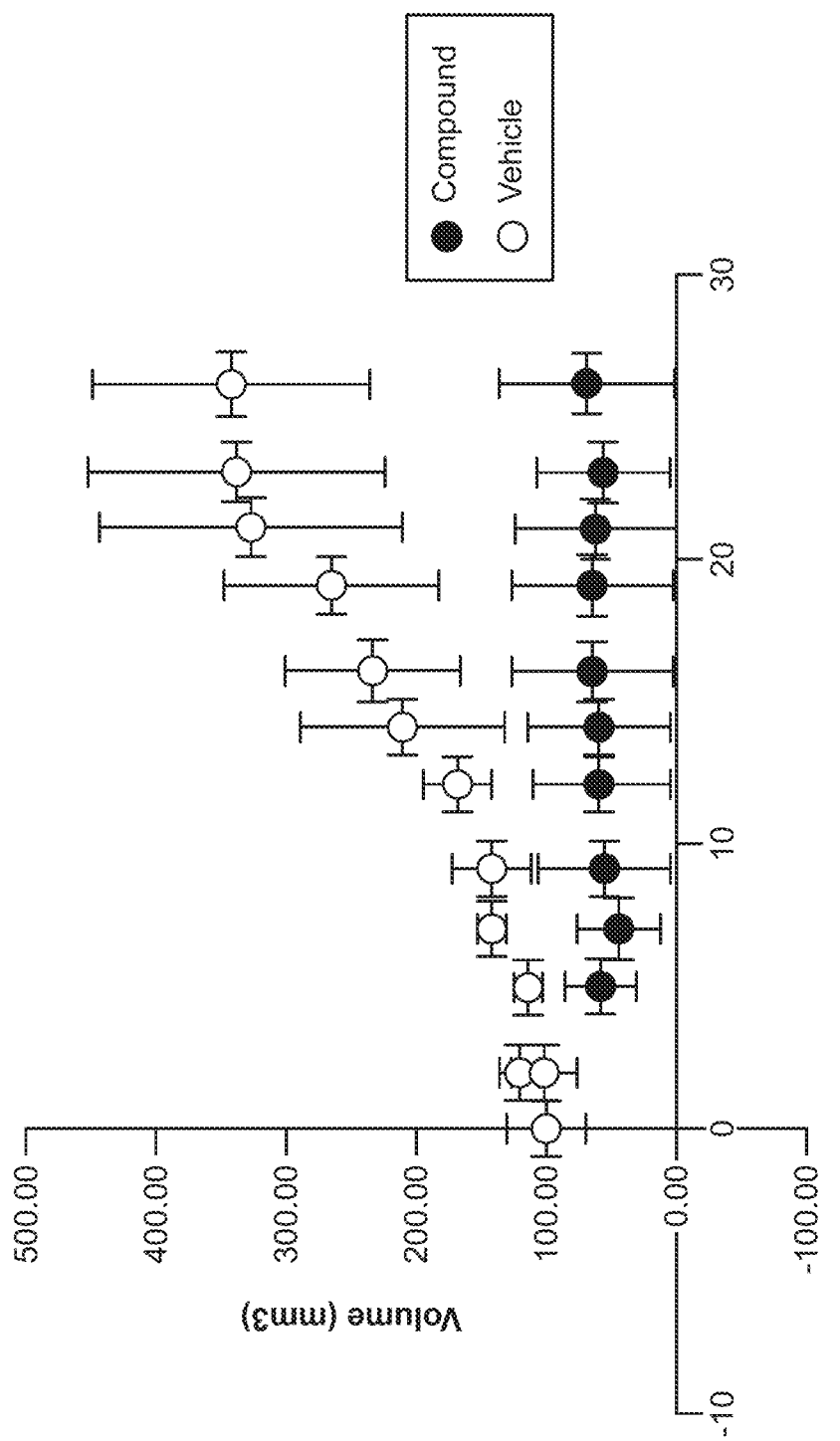
FIG. 11 provides a graph of tumor growth over time in a mouse xenograft model following treatment with [D-Trp] CJ-15,208 or vehicle (50% DMSO, 45% PEG 400, and 5% polyoxyethylene sorbitan monooleate).

FIGS. 10A, 10B, and 10C show the cellular phosphorylation status and total protein levels of three key enzymes, Erk, Akt, and PP2A following treatment with [D-Trp]CJ-15,208 at the indicated concentrations for 48 h. Cellular levels of p-Erk and p-Akt, which are the activated forms of these enzymes, did not change significantly following treatment with increasing concentrations of [D-Trp]CJ-15,208 (FIGS. 10A and 10B). The total Erk protein levels also did not decrease significantly. A significant decrease in total Akt protein levels was observed when cells were treated with the highest concentration (50 μM) of [D-Trp]CJ-15,208 (FIG. 10B. Without being bound by theory, it is thought that PP2A dephosphorylates phospho-Ser62 c-Myc, leading to c-Myc degradation in cells.[11,34] Previous studies have found a link between phosphorylation of the C-terminal tyrosine 307 of PP2A, which results in inactivation of its phosphatase activity.[16, 35, 36, 37] The level of pTyr307-PP2A in PC-3 cells was high in vehicle treated cells. [D-Trp]CJ-15,208 treatment at concentrations ≥10 μM significantly reduced p-PP2A levels in cells (FIG. 10C). Total PP2A protein levels were not significantly different than in vehicle treated cells. Taken together, the results show that treatment with [D-Trp]CJ-15, 208 according to the present technology reduces the level of p-PP2A in PC-3 cells, increases c-Myc degradation, and reduces cancer cell growth (FIG. 10D). Treatment with [D-Trp]CJ-15,208 did not have significant effects on p-Erk or p-Akt levels, but significantly reduced p-PP2A levels in a concentration dependent manner, leading to c-Myc degradation and reduction in cancer cell growth (FIGS. 10A-10D). Thus, the results demonstrate that [D-Trp]CJ,15-208 regulates a protein involved in c-Myc degradation, resulting in decreased c-Myc protein levels in prostate cancer cells and decreased cell growth.

In-Vivo Model for Prostate Cancer

An in-vivo study was performed to determine tumor growth inhibition by [D-Trp]CJ-15,208 in a mouse xenograft model. PC-3 cells were injected subcutaneously in both rear flanks of nude mice. Once tumors were established, mice were treated intraperitoneally three times per week with either vehicle (50% DMSO, 45% PEG 400, and 5% polyoxyethylene (20) sorbitan monooleate (Tween 80); 3 mice, 6 tumors) or [D-Trp]CJ-15,208 (30 mg/kg in vehicle; 2 mice, 3 tumors). Tumor volume was measured using calipers.

Results:

Mice injected with PC-3 cells underwent treatment with [D-Trp]CJ-15,208 or with vehicle as described herein. As illustrated in FIG. 10, mice treated with [D-Trp]CJ-15,208 exhibited a decrease in tumor growth compared to mice treated with vehicle treated control.

CJ-15,208 and [D-Trp]CJ-15,208 possess several advantages in regards to anti-cancer activity. They are active after oral administration and showed no evidence of toxicity in mice at a dose of 60 mg/kg in mice.[24, 25] An additional advantage is that these macrocyclic tetrapeptides appear to penetrate the blood-brain barrier in mice after systemic administration,[24, 25] which makes these compounds particularly useful for prostate cancers that metastasize to the brain.

Taken together, the data illustrates that CJ-15,208 and [D-Trp]CJ-15,208 are useful in the treatment of prostate cancer (such as advanced prostate cancer).

Anti-Breast Cancer Activity

As discussed previously herein, c-Myc is overexpressed in 30-50% of high grade breast cancer tumors, and activation of c-Myc has been reported in breast cancer progression (Fallah, Y.; Brundage, J.; Allegakoen, P.; Shajahan-Haq, A. N. MYC-Driven Pathways in Breast Cancer Subtypes. *Biomolecules* 2017, 7). Evidence indicates c-Myc overexpression contributes to developing resistance to hormonal therapy in estrogen receptor (ER) positive tumors (McNeil, C. M.; Sergio, C. M.; Anderson, L. R.; Inman, C. K.; Eggleton, S. A.; Murphy, N. C.; Millar, E. K.; Crea, P.; Kench, J. G.; Alles, M. C.; Gardiner-Garden, M.; Ormandy, C. J.; Butt, A. J.; Henshall, S. M.; Musgrove, E. A.; Sutherland, R. L. c-Myc overexpression and endocrine resistance in breast cancer. *J Steroid Biochem Mol Blot* 2006, 102, 147-155; Shajahan-Haq, A. N.; Cook, K. L.; Schwartz-Roberts, J. L.; Eltayeb, A. E.; Demas, D. M.; Warri, A. M.; Facey, C. O.; Hilakivi-Clarke, L. A.; Clarke, R. MYC regulates the unfolded protein response and glucose and glutamine uptake in endocrine resistant breast cancer. *Mol Cancer* 2014, 13, 239). c-Myc expression is also elevated in triple negative breast cancer (TNBC) compared to tumors expressing ER or HER2, and c-Myc overexpression in TNBC correlates with a poor prognosis (Horiuchi, D.; Kusdra, L.; Huskey, N. E.; Chandriani, S.; Lenburg, M. E.; Gonzalez-Angulo, A. M.; Creasman, K. J.; Bazarov, A. V.; Smyth, J. W.; Davis, S. E.; Yaswen, P.; Mills, G. B.; Esserman, L. J.; Goga, A. MYC pathway activation in triple-negative breast cancer is synthetic lethal with CDK inhibition. *J Exp Med* 2012, 209, 679-696). Thus, based on the data presented above, it is expected that CJ-15,208 and [D-Trp]CJ-15,208 will decrease cancer cell proliferation by decreasing c-Myc expression in these tumors and, therefore, are useful to treat these types of breast cancer.

In-Vitro Model for Breast Cancer

CJ-15,208 and [D-Trp]CJ-15,208 will be evaluated for their anti-proliferative activity and effects on c-Myc levels in several TNBC cell lines (BT-20, MDA-MB-468 and MDA-MB-231) as well as other breast cancer cell lines with different receptor expression patterns (MCF-7 (ER+/PR+/HER2−), SKBR-3 (ER−/PR−/HER2+), and BT-474 (ER+/PR+/HER2+)). Cells will be treated in triplicate with concentrations of the macrocyclic tetrapeptide between 0.1 and 50 µM or vehicle (control). The WST-1 reagent will be added 0-72 hours following treatment and absorbance will be measured to determine effects of the compound on cell proliferation. Cells will be treated in duplicate with vehicle (control) or the macrocyclic tetrapeptide at concentrations and a time period chosen based on the anti-proliferation studies, the cells lysed and c-Myc protein levels determined by western blot analysis. It is expected that CJ-15,208 and [D-Trp]CJ-15,208 will each decrease cancer cell proliferation in the cell lines that exhibit high levels of c-Myc (i.e., levels of c-Myc significantly greater than levels of c-Myc in normal breast cells).

In-Vivo Model for Breast Cancer

In vivo anti-proliferative activity of CJ-15,208 and [D-Trp]CJ-15,208 will be evaluated in xenograft tumor models in immunocompromised mice utilizing human breast cancer cell lines chosen based on the results of the in vitro studies described herein. Once tumors are established, mice will be treated intraperitoneally three times per week with either vehicle (50% DMSO, 45% PEG 400, and 5% Tween 80; 3 mice, 6 tumors) or [D-Trp]CJ-15,208 (30-60 mg/kg in vehicle; 2 mice, 3 tumors). Tumor volume will be measured using calipers to determine reduction in tumor proliferation compared to control mice receiving vehicle. It is expected that CJ-15,208 and [D-Trp]CJ-15,208 will each provide a significant reduction in tumor proliferation compared to the control mice.

REFERENCES

1. Karanika S, Karantanos T, Kurosaka S, Wang J, Hirayama T, Yang G, Park S, Golstov A A, Tanimoto R, Li L, et al. GLIPR1-Delta™ synergizes with docetaxel in cell death and suppresses resistance to docetaxel in prostate cancer cells. Mol Cancer 2015; 14:122.
2. Amaral T M, Macedo D, Fernandes I, Costa L. Castration-resistant prostate cancer: mechanisms, targets, and treatment. Prostate Cancer 2012; 2012:327253.
3. Ryan C J, Smith M R, de Bono J S, Molina A, Logothetis C J, de Souza P, Fizazi K, Mainwaring P, Piulats J M, Ng S, et al. Abiraterone in metastatic prostate cancer without previous chemotherapy. N. Engl J Med 2013; 368:138-48.
4. Scher H I, Fizazi K, Saad F, Taplin M E, Sternberg C N, Miller K, de Wit R, Mulders P, Chi K N, Shore N D, et al. Increased survival with enzalutamide in prostate cancer after chemotherapy. N Engl J Med 2012; 367:1187-97.
5. Gao L, Schwartzman J, Gibbs A, Lisac R, Kleinschmidt R, Wilmot B, Bottomly D, Coleman I, Nelson P, McWeeney S, et al. Androgen receptor promotes ligand-independent prostate cancer progression through c-Myc upregulation. PLoS One 2013; 8:e63563.
6. Zhang X, Morrissey C, Sun S, Ketchandji M, Nelson P S, True L D, Vakar-Lopez F, Vessella R L, Plymate S R. Androgen receptor variants occur frequently in castration resistant prostate cancer metastases. PloS one 2011; 6:e27970.
7. Vander Griend D J, Litvinov I V, Isaacs J T. Conversion of androgen receptor signaling from a growth suppressor in normal prostate epithelial cells to an oncogene in prostate cancer cells involves a gain of function in c-Myc regulation. Int J Biol Sci 2014; 10:627-42.
8. Meyer N, Penn L Z. Reflecting on 25 years with MYC. Nat Rev Cancer 2008; 8:976-90.
9. Miller D M, Thomas S D, Islam A, Muench D, Sedoris K. c-Myc and cancer metabolism. Clin Cancer Res 2012; 18:5546-53.
10. Westermarck J, Hahn W C. Multiple pathways regulated by the tumor suppressor PP2A in transformation. Trends Mol Med 2008; 14:152-60.
11. Sears R C. The life cycle of C-myc: from synthesis to degradation. Cell Cycle 2004; 3:1133-7.
12. Tibbitts D C, Escamilla-Powers J R, Zhang X, Sears R C. Studying c-Myc serine 62 phosphorylation in leukemia cells: concern over antibody cross-reactivity. Blood 2012; 119:5334-5.
13. Sears R, Nuckolls F, Haura E, Taya Y, Tamai K, Nevins J R. Multiple Ras-dependent phosphorylation pathways regulate Myc protein stability. Genes Dev 2000; 14:2501-14.
14. Bernard D, Pourtier-Manzanedo A, Gil J, Beach D H. Myc confers androgen-independent prostate cancer cell growth. J Clin Invest 2003; 112:1724-31.
15. Ryan C J, Molina A, Griffin T. Abiraterone in metastatic prostate cancer. N Engl J Med 2013; 368:1458-9.
16. Mukhopadhyay A, Tabanor K, Chaguturu R, Aldrich J V. Targeting inhibitor 2 of protein phosphatase 2A as a therapeutic strategy for prostate cancer treatment. Cancer Biol Ther 2013; 14:962-72.
17. Nadiminty N, Tummala R, Liu C, Lou W, Evans C P, Gao A C. NF-kappaB2/p52:c-Myc:hnRNPA1 Pathway Regulates Expression of Androgen Receptor Splice Variants and Enzalutamide Sensitivity in Prostate Cancer. Mol Cancer Ther 2015; 14:1884-95.
18. Sivertsen A, Torfoss V, Isaksson J, Ausbacher D, Anderssen T, Brandsdal B O, Havelkova M, Skjorholm A E, Strom M B. Anticancer potency of small linear and cyclic tetrapeptides and pharmacokinetic investigations of peptide binding to human serum albumin. J Peptide Sci 2014; 20:279-91.
19. Murray B C, Peterson M T, Fecik R A. Chemistry and biology of tubulysins: antimitotic tetrapeptides with activity against drug resistant cancers. Nat Prod Rep 2015; 32:654-62.
20. Neviani P, Perrotti D. SETting OP449 into the PP2A-activating drug family. Clin Cancer Res 2014; 20:2026-8.
21. Saito T, Hirai H, Kim Y J, Kojima Y, Matsunaga Y, Nishida H, Sakakibara T, Suga O, Sujaku T, Kojima N. CJ-15,208, a novel kappa opioid receptor antagonist from a fungus, Ctenomyces serratus ATCC15502. J Antibiot (Tokyo) 2002; 55:847-54.
22. Ross N C, Kulkarni S S, McLaughlin J P, Aldrich J V. Synthesis of CJ-15,208, a novel kappa-opioid receptor antagonist. Tetrahedron Lett 2010; 51:5020-3.
23. Ross N C, Reilley K J, Murray T F, Aldrich J V, McLaughlin J P. Novel opioid cyclic tetrapeptides: Trp isomers of CJ-15,208 exhibit distinct opioid receptor agonism and short-acting kappa opioid receptor antagonism. Br J Pharmacol 2012; 165:1097-108.
24. Aldrich J V, Senadheera S N, Ross N C, Ganno M L, Eans S O, McLaughlin J P. The macrocyclic peptide natural product CJ-15,208 is orally active and prevents reinstatement of extinguished cocaine-seeking behavior. J Nat Prod 2013; 76:433-8.
25. Eans S O, Ganno M L, Reilley K J, Patkar K A, Senadheera S N, Aldrich J V, McLaughlin J P. The macrocyclic tetrapeptide [D-Trp]CJ-15,208 produces short-acting kappa opioid receptor antagonism in the CNS after oral administration. Br J Pharmacol 2013; 169:426-36.
26. Fichna J, Janecka A. Opioid peptides in cancer. Cancer Metastasis Rev 2004; 23:351-66.
27. Gach K, Wyrebska A, Fichna J, Janecka A. The role of morphine in regulation of cancer cell growth. Naunyn Schmiedebergs Arch Pharmacol 2011; 384:221-30.
28. Moon T D. The effect of opiates upon prostatic carcinoma cell growth. Biochem Biophys Res Commun 1988; 153:722-7.
29. Kuzumaki N, Suzuki A, Narita M, Hosoya T, Nagasawa A, Imai S, Yamamizu K, Morita H, Nagase H, Okada Y, et al. Effect of kappa-opioid receptor agonist on the growth of non-small cell lung cancer (NSCLC) cells. Br J Cancer 2012; 106:1148-52.
30. Yeh E, Cunningham M, Arnold H, Chasse D, Monteith T, Ivaldi G, Hahn W C, Stukenberg P T, Shenolikar S, Uchida T, et al. A signalling pathway controlling c-Myc degradation that impacts oncogenic transformation of human cells. Nat Cell Biol 2004; 6:308-18.
31. Patkar K A, Yan X, Murray T F, Aldrich J V. [NabenzylTyr1,cyclo(D-Asp5,Dap8)]-dynorphin A-(1-11) NH2 cyclized in the "address" domain is a novel kappa-opioid receptor antagonist. J Med Chem 2005; 48:4500-3.
32. Arttamangkul S, Ishmael J E, Murray T F, Grandy D K, DeLander G E, Kieffer B L, Aldrich J V. Synthesis and opioid activity of conformationally constrained dynorphin A analogues. 2. Conformational constraint in the "address" sequence. J Med Chem 1997; 40:1211-8.
33. Pelengaris S, Khan M, Evan G. c-MYC: more than just a matter of life and death. Nat Rev Cancer 2002; 2:764-76.
34. Oaks J J, Santhanam R, Walker C J, Roof S, Harb J G, Ferenchak G, Eisfeld A K, Van Brocklyn J R, Briesewitz R, Saddoughi S A, et al. Antagonistic activities of the immunomodulator and PP2A-activating drug FTY720 (Fingolimod, Gilenya) in Jak2-driven hematologic malignancies. Blood 2013; 122:1923-34.
35. Chen J, Martin B L, Brautigan D L. Regulation of protein serine-threonine phosphatase type-2A by tyrosine phosphorylation. Science 1992; 257:1261-4.
36. Neviani P, Santhanam R, Trotta R, Notari M, Blaser B W, Liu S, Mao H, Chang J S, Galietta A, Uttam A, et al. The tumor suppressor PP2A is functionally inactivated in blast crisis CIVIL through the inhibitory activity of the BCR/ABL-regulated SET protein. Cancer Cell 2005; 8:355-68.
37. Lu J J, Meng L H, Shankavaram U T, Zhu C H, Tong L J, Chen G, Lin L P, Weinstein J N, Ding J. Dihydroartemisinin accelerates c-MYC oncoprotein degradation and induces apoptosis in c-MYC-overexpressing tumor cells. Biochem Pharmacol 2010; 80:22-30.
38. Zhang J Y, Tao L Y, Liang Y J, Yan Y Y, Dai C L, Xia X K, She Z G, Lin Y C, Fu L W. Secalonic acid D induced leukemia cell apoptosis and cell cycle arrest of G(1) with involvement of GSK-3beta/beta-catenin/c-Myc pathway. Cell Cycle 2009; 8:2444-50.
39. Thamilselvan V, Menon M, Thamilselvan S. Anticancer efficacy of deguelin in human prostate cancer cells targeting glycogen synthase kinase-3 beta/beta-catenin pathway. Int J Cancer 2011; 129:2916-27.
40. Huang H L, Weng H Y, Wang L Q, Yu C H, Huang Q J, Zhao P P, Wen J Z, Zhou H, Qu L H. Triggering Fbw7-mediated proteasomal degradation of c-Myc by oridonin induces cell growth inhibition and apoptosis. Mol Cancer Ther 2012; 11:1155-65.
41. Zhang Y, Guo Z, Xu L. Tributyltin induces a G2/M cell cycle arrest in human amniotic cells via PP2A inhibition-mediated inactivation of the ERK1/2 cascades. Environ Toxicol Pharmacol 2014; 37:812-8.
42. Song A, Ye J, Zhang K, Sun L, Zhao Y, Yu H. Lentiviral vector-mediated siRNA knockdown of c-MYC: cell growth inhibition and cell cycle arrest at G2/M phase in Jijoye cells. Biochem Genet 2013; 51:603-17.
43. Lin H P, Lin C Y, Huo C, Hsiao P H, Su L C, Jiang S S, Chan T M, Chang C H, Chen L T, Kung H J, et al. Caffeic acid phenethyl ester induced cell cycle arrest and growth inhibition in androgen-independent prostate cancer cells via regulation of Skp2, p53, p21Cip1 and p27Kip1. Oncotarget 2015; 6:6684-707.
44. Jingushi K, Nakamura T, Takahashi-Yanaga F, Matsuzaki E, Watanabe Y, Yoshihara T, Morimoto S, Sasaguri T. Differentiation-inducing factor-1 suppresses the expression of c-Myc in the human cancer cell lines. J Pharmacol Sci 2013; 121:103-9.
45. Akinyeke T O, Stewart L V. Troglitazone suppresses c-Myc levels in human prostate cancer cells via a PPAR-gamma-independent mechanism. Cancer Biol Ther 2011; 11:1046-58.
46. Sampson N, Neuwirt H, Puhr M, Klocker H, Eder I E. In vitro model systems to study androgen receptor signaling in prostate cancer. Endocr Relat Cancer 2013; 20:R49-64.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A method comprising administering at least one of cyclo[Phe-D-Pro-Phe-Trp] and cyclo[Phe-D-Pro-Phe-D-Trp] or a pharmaceutically acceptable salt thereof to a subject suffering from prostate cancer or breast cancer.

B. The method of Paragraph A, wherein the method comprises administering an effective amount of at least one of cyclo[Phe-D-Pro-Phe-Trp] and cyclo[Phe-D-Pro-Phe-D-Trp] or a pharmaceutically acceptable salt thereof to the subject.

C. The method of Paragraph A or Paragraph B, wherein the prostate cancer comprises at least one oncogenic mutation found in a PC-3 cell line, a LNCaP cell line, a 22Rv1 cell line, a DU145 cell line, or a combination of any two or more thereof.

D. The method of any one of Paragraphs A-C, wherein the breast cancer comprises triple negative breast cancer.

E. The method of any one of Paragraphs A-D, wherein the breast cancer comprises at least one oncogenic mutation found in a BT-20 cell line, a MDA-MB-468 cell line, a MDA-MB-231 cell line, a MCF-7 cell line, a SKBR-3 cell line, a BT-474 cell line, or a combination of any two or more thereof F. The method of any one of Paragraphs A-E, wherein administering comprises oral administration or parenteral administration.

G. The method of any one of Paragraphs A-F, wherein administering comprises at least one of subcutaneous administration, intravenous administration, and oral administration.

H. The method of any one of Paragraphs A-G, wherein the method comprises administering cyclo[Phe-D-Pro-Phe-Trp] or a pharmaceutically acceptable salt thereof.

I. The method of any one of Paragraphs A-H, wherein the method comprises administering cyclo[Phe-D-Pro-Phe-D-Trp] or a pharmaceutically acceptable salt thereof.

J. The method of any one of Paragraphs A-I, wherein the method comprises administering a composition comprising at least one of cyclo[Phe-D-Pro-Phe-Trp] and cyclo[Phe-D-Pro-Phe-D-Trp] or a pharmaceutically acceptable salt thereof and a pharmaceutically acceptable carrier.

K. The method of Paragraph J, wherein the composition is formulated for oral administration or parenteral administration.

L. The method of Paragraph J or Paragraph K, wherein the composition is formulated for at least one of subcutaneous administration and intravenous administration.

M. The method of any one of Paragraphs J-L, wherein the pharmaceutically acceptable carrier comprises saline.
N. The method of any one of Paragraphs J-M, wherein the pharmaceutically acceptable carrier comprises polyethylene glycol, a polyethylene glycol fatty acid monoester, a polyethoxylene sorbitan ester, or a combination of any two or more thereof
O. The method of any one of Paragraphs J-N, wherein the composition is a liquid formulation comprising about 0.1 mg/mL to about 50 mg/mL of the at least one of cyclo[Phe-D-Pro-Phe-Trp] and cyclo[Phe-D-Pro-Phe-D-Trp] or a pharmaceutically acceptable salt thereof
P. The method of any one of Paragraphs J-O, wherein the composition is a pharmaceutical composition.
Q. The method of any one of Paragraphs A-P, wherein the method comprises administering to the subject about 1 mg to about 150 mg of the at least one of cyclo[Phe-D-Pro-Phe-Trp] and cyclo[Phe-D-Pro-Phe-D-Trp] per kilogram of the subject.
R. The method of any one of Paragraphs A-Q, wherein the method comprises administering to the subject from about 1 to about 7 times per week.
S. Use of at least one of cyclo[Phe-D-Pro-Phe-Trp] and cyclo[Phe-D-Pro-Phe-D-Trp] or a pharmaceutically acceptable salt thereof or a composition comprising at least one of cyclo[Phe-D-Pro-Phe-Trp] and cyclo[Phe-D-Pro-Phe-D-Trp] or a pharmaceutically acceptable salt thereof and a pharmaceutically acceptable carrier for treating a subject suffering from prostate cancer or breast cancer.
T. Use of an effective amount of at least one of cyclo[Phe-D-Pro-Phe-Trp] and cyclo[Phe-D-Pro-Phe-D-Trp] or a pharmaceutically acceptable salt thereof or a composition comprising an effective amount of at least one of cyclo[Phe-D-Pro-Phe-Trp] and cyclo[Phe-D-Pro-Phe-D-Trp] or a pharmaceutically acceptable salt thereof and a pharmaceutically acceptable carrier for treating a subject suffering from prostate cancer or breast cancer.
U. The use of Paragraph S or the use of Paragraph T, wherein prostate cancer comprises at least one oncogenic mutation found in a PC-3 cell line, a LNCaP cell line, a 22Rv1 cell line, a DU145 cell line, or a combination of any two or more thereof.
V The use of any one of Paragraphs S-U, wherein the breast cancer comprises triple negative breast cancer.
W. The use of any one of Paragraphs S-V, wherein the breast cancer comprises at least one oncogenic mutation found in a BT-20 cell line, a MDA-MB-468 cell line, a MDA-MB-231 cell line, a MCF-7 cell line, a SKBR-3 cell line, a BT-474 cell line, or a combination of any two or more thereof
X. The use of any one of Paragraphs S-W, wherein the use comprises parenteral administration or oral administration.
Y The use of any one of Paragraphs S-X, wherein the use comprises at least one of subcutaneous administration, intravenous administration, and oral administration.
Z. The use of any one of Paragraphs S-Y, wherein the composition is formulated for oral administration or parenteral administration.
AA. The use of any one of Paragraphs S-Z, wherein the composition is formulated for at least one of subcutaneous administration, intravenous administration, and oral administration.
AB. The use of any one of Paragraphs S-AA, wherein the pharmaceutically acceptable carrier comprises saline.
AC. The use of any one of Paragraphs S-AB, wherein the pharmaceutically acceptable carrier comprises polyethylene glycol, a polyethylene glycol fatty acid monoester, a polyethoxylene sorbitan ester, or a combination of any two or more thereof.
AD. The use of any one of Paragraphs S-AC, wherein the composition is a liquid formulation comprising about 0.1 mg/mL to about 50 mg/mL of the at least one of cyclo[Phe-D-Pro-Phe-Trp] and cyclo[Phe-D-Pro-Phe-D-Trp] or a pharmaceutically acceptable salt thereof.
AE. The use of any one of Paragraphs S-AD, wherein the composition is a pharmaceutical composition.
AF. The use of any one of Paragraphs S-AE, wherein the method comprises administering to the subject about 1 mg to about 150 mg of the at least one of cyclo[Phe-D-Pro-Phe-Trp] and cyclo[Phe-D-Pro-Phe-D-Trp] per kilogram of the subject.
AG. The use of any one of Paragraphs S-AF, wherein the use comprises administering to the subject at least one of cyclo[Phe-D-Pro-Phe-Trp] and cyclo[Phe-D-Pro-Phe-D-Trp] or a pharmaceutically acceptable salt thereof from about 1 to about 7 times per week.
AH. At least one of cyclo[Phe-D-Pro-Phe-Trp] and cyclo[Phe-D-Pro-Phe-D-Trp] or a pharmaceutically acceptable salt thereof for use in a medicament for the treatment of prostate cancer or breast cancer in a subject.
AI. An effective amount of at least one of cyclo[Phe-D-Pro-Phe-Trp] and cyclo[Phe-D-Pro-Phe-D-Trp] or a pharmaceutically acceptable salt thereof for use in a medicament for the treatment of prostate cancer or breast cancer in a subject.
AJ. The medicament of Paragraph AH or the use of Paragraph AI, wherein prostate cancer comprises at least one oncogenic mutation found in a PC-3 cell line, a LNCaP cell line, a 22Rv1 cell line, a DU145 cell line, or a combination of any two or more thereof.
AK. The medicament of any one of Paragraphs AH-AJ, wherein the breast cancer comprises triple negative breast cancer.
AL. The medicament of any one of Paragraphs AH-AK, wherein the breast cancer comprises at least one oncogenic mutation found in a BT-20 cell line, a MDA-MB-468 cell line, a MDA-MB-231 cell line, a MCF-7 cell line, a SKBR-3 cell line, a BT-474 cell line, or a combination of any two or more thereof.
AM. The medicament of any one of Paragraphs AH-AL, wherein the composition is formulated for oral administration or parenteral administration.
AN. The medicament of any one of Paragraphs AH-AM, wherein the medicament is formulated for at least one of subcutaneous administration, intravenous administration, and oral administration.
AO. The medicament of any one of Paragraphs AH-AN, wherein the medicament comprises a pharmaceutically acceptable carrier.
AP. The medicament of any one of Paragraphs AH-AO, wherein the medicament comprises saline.
AQ. The medicament of any one of Paragraphs AH-AP, wherein the medicament comprises polyethylene glycol, a polyethylene glycol fatty acid monoester, a polyethoxylene sorbitan ester, or a combination of any two or more thereof
AR. The medicament of any one of Paragraphs AH-AQ, wherein the medicament is a liquid formulation comprising about 0.1 mg/mL to about 50 mg/mL of the at least one of cyclo[Phe-D-Pro-Phe-Trp] and cyclo[Phe-D-Pro-Phe-D-Trp] or a pharmaceutically acceptable salt thereof.

Other embodiments are set forth in the following claims, along with the full scope of equivalents to which such claims are entitled.

What is claimed is:

1. A method comprising administering at least one of cyclo[Phe-D-Pro-Phe-Trp] and cyclo[Phe-D-Pro-Phe-D-Trp] or a pharmaceutically acceptable salt thereof to a subject suffering from prostate cancer or breast cancer.

2. The method of claim 1, wherein the method comprises administering an effective amount of at least one of cyclo[Phe-D-Pro-Phe-Trp] and cyclo[Phe-D-Pro-Phe-D-Trp] or a pharmaceutically acceptable salt thereof to the subject, wherein the effective amount is effective in treating the prostate cancer or the breast cancer.

3. The method of claim 1, wherein the prostate cancer comprises at least one oncogenic mutation found in a PC-3 cell line, a LNCaP cell line, a 22Rv1 cell line, a DU145 cell line, or a combination of any two or more thereof.

4. The method of claim 1, wherein the breast cancer comprises triple negative breast cancer.

5. The method of claim 1, wherein the breast cancer comprises at least one oncogenic mutation found in a BT-20 cell line, a MDA-MB-468 cell line, a MDA-MB-231 cell line, a MCF-7 cell line, a SKBR-3 cell line, a BT-474 cell ine, or a combination of any two or more thereof.

6. The method of claim 1, wherein administering comprises oral administration or parenteral administration.

7. The method of claim 1, wherein administering comprises at least one of subcutaneous administration, intravenous administration, and oral administration.

8. The method of claim 1, wherein the method comprises administering cyclo[Phe-D-Pro-Phe-Trp] or a pharmaceutically acceptable salt thereof.

9. The method of claim 1, wherein the method comprises administering cyclo[Phe-D-Pro-Phe-D-Trp] or a pharmaceutically acceptable salt thereof.

10. The method of claim 1, wherein the method comprises administering a composition comprising at least one of cyclo[Phe-D-Pro-Phe-Trp] and cyclo[Phe-D-Pro-Phe-D-Trp] and a pharmaceutically acceptable carrier.

11. The method of claim 10, wherein the composition is formulated for oral administration or parenteral administration.

12. The method of claim 10, wherein the composition is formulated for at least one of subcutaneous administration and intravenous administration.

13. The method of claim 10, wherein the pharmaceutically acceptable carrier comprises saline.

14. The method of claim 10, wherein the pharmaceutically acceptable carrier comprises polyethylene glycol, a polyethylene glycol fatty acid monoester, a polyethoxylene sorbitan ester, or a combination of any two or more thereof.

15. The method of claim 10, wherein the composition is a liquid formulation comprising about 0.1 mg/mL to about 50 mg/mL of the at least one of cyclo[Phe-D-Pro-Phe-Trp] and cyclo[Phe-D-Pro-Phe-D-Trp] or a pharmaceutically acceptable salt thereof.

16. The method of claim 1, wherein the method comprises administering to the subject about 1 mg to about 150 mg of the at least one of cyclo[Phe-D-Pro-Phe-Trp] and cyclo[Phe-D-Pro-Phe-D-Trp] per kilogram of the subject.

17. The method of claim 1, wherein the method comprises administering to the subject from about 1 to about 7 times per week.

18. The method of claim 2, wherein the prostate cancer comprises at least one oncogenic mutation found in a PC-3 cell line, a LNCaP cell line, a 22Rv1 cell line, a DU145 cell line, or a combination of any two or more thereof.

19. The method of claim 2, wherein the breast cancer comprises triple negative breast cancer.

20. The method of claim 2, wherein the breast cancer comprises at least one oncogenic mutation found in a BT-20 cell line, a MDA-MB-468 cell line, a MDA-MB-231 cell line, a MCF-7 cell line, a SKBR-3 cell line, a BT-474 cell line, or a combination of any two or more thereof.

* * * * *

UNITED STATES PATENT AND TRADEMARK OFFICE
CERTIFICATE OF CORRECTION

PATENT NO. : 11,510,964 B2
APPLICATION NO. : 17/072409
DATED : November 29, 2022
INVENTOR(S) : Jane Aldrich, Archana Mukhopadhyay and Laura E. Hanold It is certified that error appears in the above-identified patent and that said Letters Patent is hereby corrected as shown below:

In the Claims

At Column 29, Line 7, Claim 5:
Delete "ine" and replace with --line--

Signed and Sealed this
Ninth Day of May, 2023

Katherine Kelly Vidal
*Director of the United States Patent and Trademark Office*